(12) United States Patent
Ishihara

(10) Patent No.: US 8,606,350 B2
(45) Date of Patent: Dec. 10, 2013

(54) ENDOSCOPE APPARATUS

(75) Inventor: Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 1367 days.

(21) Appl. No.: 11/190,316

(22) Filed: Jul. 27, 2005

(65) Prior Publication Data

US 2006/0025692 A1    Feb. 2, 2006

(30) Foreign Application Priority Data

Jul. 30, 2004  (JP) ................................ 2004-223861
Jul. 19, 2005  (JP) ................................ 2005-208828

(51) Int. Cl.
   *A61B 6/00*    (2006.01)
(52) U.S. Cl.
   USPC .......................................... 600/476; 600/407
(58) Field of Classification Search
   USPC ....................................................... 600/476
   See application file for complete search history.

(56) References Cited

U.S. PATENT DOCUMENTS

| | | | |
|---|---|---|---|
| 2,764,148 A * | 9/1956 | Sheldon ......................... | 600/109 |
| 4,489,727 A | 12/1984 | Matsuo et al. | |
| 4,744,040 A * | 5/1988 | Kawata et al. ................ | 702/159 |
| 5,219,345 A * | 6/1993 | Potter ............................. | 606/15 |
| 5,608,451 A | 3/1997 | Konno et al. | |
| 5,749,830 A | 5/1998 | Kaneko et al. | |
| 5,885,531 A * | 3/1999 | Heffelfinger et al. ....... | 422/82.05 |
| 5,983,120 A * | 11/1999 | Groner et al. ................. | 600/310 |
| 6,004,273 A | 12/1999 | Sakamoto et al. | |
| 6,388,702 B1 * | 5/2002 | Konomura et al. ............ | 348/74 |
| 2002/0007110 A1 | 1/2002 | Irion | |
| 2002/0154305 A1 * | 10/2002 | Jung et al. ..................... | 356/419 |
| 2002/0166946 A1 * | 11/2002 | Iizuka et al. ................ | 250/201.2 |
| 2002/0168096 A1 * | 11/2002 | Hakamata et al. ............ | 382/132 |
| 2002/0183623 A1 * | 12/2002 | Tang et al. ..................... | 600/476 |
| 2003/0040659 A1 * | 2/2003 | Kazakevich ................. | 600/167 |
| 2003/0120289 A1 * | 6/2003 | McGuckin et al. ........... | 606/151 |
| 2003/0163025 A1 | 8/2003 | Kaji | |
| 2003/0174205 A1 * | 9/2003 | Amling et al. .................. | 348/65 |
| 2006/0025692 A1 | 2/2006 | Ishihara | |
| 2007/0197874 A1 | 8/2007 | Ishihara | |

FOREIGN PATENT DOCUMENTS

| | | |
|---|---|---|
| JP | Hei-7-155285 | 6/1995 |
| JP | 08-254659 | 10/1996 |
| JP | Hei-10-243920 | 9/1998 |
| JP | 11-148897 | 6/1999 |

(Continued)

OTHER PUBLICATIONS

Masafumi, JP 61-155909 translated abstract.*

(Continued)

*Primary Examiner* — Unsu Jung
*Assistant Examiner* — Saurel J Selkin
(74) *Attorney, Agent, or Firm* — Scully, Scott, Murphy & Presser, P.C.

(57) ABSTRACT

The present invention provides an endoscope apparatus that includes a laser light source for generating excitation light, an endoscopy scope having an irradiation section for irradiating excitation light at an end portion thereof, a CCD incorporating an intensifier for detecting fluorescence generated by excitation light in a tissue, a fluorescence-image generating unit for generating a fluorescence image signal based on a fluorescence signal from the CCD incorporating an intensifier, a distance-measuring unit for generating a distance signal corresponding to the distance between the irradiation section and the tissue, and an amount-of-fluorescence calculating unit for correcting the fluorescence signal with the distance signal to calculate an amount of fluorescence not affected by changes in the distance.

26 Claims, 19 Drawing Sheets

(56) References Cited

FOREIGN PATENT DOCUMENTS

| | | |
|---|---|---|
| JP | 2002-065581 | 3/2002 |
| JP | 2003-036436 | 2/2003 |
| JP | 2003-334161 | 11/2003 |
| JP | 2004-187716 A | 7/2004 |
| JP | 2005-013279 | 1/2005 |
| JP | 2005-118133 | 5/2005 |
| JP | 2006-061683 | 3/2006 |
| JP | 2007-222381 | 9/2007 |
| WO | WO-0054652 A1 * | 9/2000 |

OTHER PUBLICATIONS

International Search Report dated May 13, 2008 issued in corresponding International Application No. PCT/JP2008/054748.
U.S. Non-Final Office Action dated Dec. 18, 2012 issued in corresponding U.S. Appl. No. 12/531,163.
U.S. Office Action dated Jul. 9, 2013 issued in U.S. Appl. No. 12/531,163.

* cited by examiner

ENDOSCOPE APPARATUS

BACKGROUND OF THE INVENTION

1. Field of the Invention

The present invention relates to endoscope apparatuses for directly observing a body cavity or the lumen of an organ, and particularly to an endoscope apparatus for illuminating a tissue with excitation light to allow an affected site to be observed for diagnosis using fluorescence generated by the tissue.

2. Description of Related Art

Technologies for generating a fluorescence image by detecting autofluorescence from a tissue or fluorescence generated by a chemical agent administered to the tissue with an endoscope apparatus in order to examine biological tissues for degeneration or disease such as cancer based on this fluorescence image are known.

Endoscope apparatuses for performing fluoroscopy are described in, for example, Japanese Unexamined Patent Application Publication No. Hei-7-155285 and Japanese Unexamined Patent Application Publication No. Hei-10-243920.

The endoscope apparatus described in Japanese Unexamined Patent Application Publication No. Hei-7-155285 has a structure for selectively displaying a normal endoscopic image or a fluorescence image depending on the amount of light in the fluorescence image. With this structure, not only can the image be easily switched between an endoscopic image and a fluorescence image, but a lesion can be distinguished from normal tissue according to the amount of light in the fluorescence image for successful fluoroscopy of the lesion.

The endoscope apparatus described in Japanese Unexamined Patent Application Publication No. Hei-10-243920 has a structure for allowing a normal endoscopic image and a fluorescence image to be observed, as well as allowing the distance between an excitation-light irradiating section and a tissue to be measured and the output of an excitation light source to be adjusted according to the measured distance. With this structure, a fluorescence-detecting unit enables fluoroscopy with constant gain regardless of the distance between the excitation-light irradiating section and the tissue.

BRIEF SUMMARY OF THE INVENTION

The present invention provides the following solutions.

According to a first aspect, the present invention provides an endoscope apparatus including: a light source unit including at least one light source generating illumination light and excitation light; an endoscopy scope having, at an end portion thereof, an irradiation section for irradiating the illumination light and the excitation light; a reflected-light imaging unit for detecting reflected light generated as a result of the illumination light being reflected at a tissue; an endoscopic-image generating unit for generating an endoscopic image signal based on a reflected-light signal from the reflected-light imaging unit; a fluorescence-detecting unit for detecting fluorescence generated in the tissue by the excitation light; a fluorescence-image generating unit for generating a fluorescence image signal based on a fluorescence signal from the fluorescence-detecting unit; a distance-measuring unit for generating a distance signal corresponding to a distance between the irradiation section and the tissue; and a characteristic-value calculating unit for correcting the fluorescence signal or the fluorescence image signal with the distance signal to calculate a characteristic value of the fluorescence that is not influenced by changes in the distance.

According to the first aspect of the present invention, the illumination light generated by the light source unit is irradiated via the irradiation section of the endoscopy scope to the tissue. The illumination light is reflected or diffused at the tissue to form reflected light, which then enters the reflected-light imaging unit. The endoscopic-image generating unit generates the endoscopic image signal based on the reflected light detected by the reflected-light imaging unit.

On the other hand, the excitation light generated by the light source unit is irradiated via the irradiation section of the endoscopy scope to the tissue. The irradiated excitation light excites phosphor, such as fluorochrome contained in a lesion, to generate fluorescence. The fluorescence-detecting unit detects the generated fluorescence to generate the fluorescence signal according to the amount of fluorescence. The fluorescence-image generating unit generates the fluorescence image signal based on this fluorescence signal and displays it on, for example, a monitor.

In this case, even with the same tissue, the characteristic value, such as the amount of fluorescence or the size, changes depending on the distance between the irradiation section of the endoscopy scope and the tissue. According to the present invention, the distance-measuring unit generates the distance signal corresponding to the distance between the irradiation section and the tissue. The characteristic-value calculating unit corrects the fluorescence signal or the fluorescence image signal with this distance signal to calculate the characteristic value of fluorescence that is not influenced by the distance between the irradiation section and the tissue. In this manner, since a characteristic value not affected by the above-described distance is indicated, quantitative diagnosis of the lesion can be made for improved diagnostic accuracy.

The distance-measuring unit should be capable of measuring the above-described distance preferably in a non-contact manner because the endoscope apparatus is used in a body cavity.

In the first aspect of the present invention, it is preferable that the characteristic value be the amount of fluorescence.

This allows the amount of the substance generating fluorescence in a lesion such as cancer to be obtained quantitatively, contributing to an accurate diagnosis of the degree of the lesion.

In the first aspect of the present invention, it is preferable that the characteristic value be the size of a fluorescence image.

This allows the region of the substance generating fluorescence in a lesion such as cancer to be obtained quantitatively, contributing to an accurate diagnosis of the extent of the lesion.

According to a second aspect, the present invention provides an endoscope apparatus including: a light source unit including at least one light source generating illumination light and excitation light; an endoscopy scope having, at an end portion thereof, an irradiation section for irradiating the illumination light and the excitation light; a reflected-light imaging unit for detecting reflected light generated as a result of the illumination light being reflected at a tissue; an endoscopic-image generating unit for generating an endoscopic image signal based on a reflected-light signal from the reflected-light imaging unit; a fluorescence-detecting unit for detecting fluorescence generated in the tissue by the excitation light; a fluorescence-image generating unit for generating a fluorescence image signal based on a fluorescence signal from the fluorescence-detecting unit; a distance-measuring unit for generating a distance signal corresponding to a distance between the irradiation section and the tissue; a distal optical system unit for supporting an end of a transmitting member for transmitting the fluorescence to the fluorescence-detecting unit and the irradiation section, the distal optical system unit being provided so as to be movable in an optical-axis direction with respect to the endoscopy scope; and a driving unit for moving the distal optical system unit according to the distance signal from the distance-measuring unit.

According to the second aspect of the present invention, the illumination light generated by the light source unit is irradiated via the irradiation section of the endoscopy scope to the tissue. The illumination light is reflected or diffused at the tissue to form reflected light, which then enters the reflected-light imaging unit. The endoscopic-image generating unit generates the endoscopic image signal based on the reflected light detected by the reflected-light imaging unit.

On the other hand, the excitation light generated by the light source unit is irradiated via the irradiation section of the endoscopy scope to the tissue. The irradiated excitation light excites phosphor, such as fluorochrome contained in a lesion, to generate fluorescence. The fluorescence-detecting unit detects the generated fluorescence to generate the fluorescence signal according to the amount of fluorescence. The fluorescence-image generating unit generates the fluorescence image signal based on this fluorescence signal and displays it on, for example, a monitor.

In this case, even with the same tissue, the characteristic value, such as the amount of fluorescence or the size, changes depending on the distance between the irradiation section of the endoscopy scope and the tissue. According to the present invention, the distance-measuring unit generates the distance signal corresponding to the distance between the irradiation section and the tissue. With this distance signal, the driving unit moves the distal optical system unit supporting the end of the transmitting member for transmitting fluorescence, and thus the irradiation section thereof, to maintain a constant distance between the irradiation section and the tissue. Since fluoroscopy is performed with a constant distance always ensured in this manner, quantitative diagnosis of the lesion can be made for improved diagnostic accuracy.

In the first and second aspects of the present invention, it is preferable that an image superimposing unit for combining the endoscopic image signal and the fluorescence image signal be further included.

As described above, since the image superimposing unit combines the endoscopic image signal and the fluorescence image signal, a fluorescence image showing, for example, a lesion can be superimposed on an endoscopic image showing a normal external view. For this reason, the region where a lesion in the tissue exists can be displayed in association with the external view. This allows the lesion to be located correctly.

In the first and second aspects of the present invention, it is preferable that the distance-measuring unit generate the distance signal based on a ratio between an intensity of the reflected-light signal and an intensity of reflected light at a predetermined distance.

With this structure, the intensity of reflected light changes depending on the distance between the irradiation section and the tissue. By taking the ratio between the intensity of reflected light, which changes depending on this distance, and the intensity of reflected light at the predetermined distance as a reference, a distance signal indicating the ratio of the current distance between the irradiation section and the tissue to the predetermined distance as the reference is generated.

As described above, since a signal corresponding to the distance between the irradiation section and the tissue can be obtained based on the intensity of reflected light from the tissue just by setting the reflected-light intensity at the predetermined distance, a device for distance measurement can be omitted. This simplifies the structure of the endoscopy scope and allows the endoscopy scope to be manufactured at low cost.

In the first and second aspects of the present invention, it is preferable that the distance-measuring unit use ultrasound.

In the first and second aspects of the present invention, it is preferable that the distance-measuring unit use microwaves.

For the structure using ultrasound, it is preferable that the distance-measuring unit detect an output of ultrasound reflected from the tissue and calculate the distance to the tissue based on calibration data produced by presetting a relationship between the output and the distance.

In the first and second aspects of the present invention, it is preferable that the distance-measuring unit use light.

For the structure using light, it is preferable that the light be a laser beam.

Since the distance can be measured in a non-contact manner, safety is increased when the endoscope apparatus is used in a body cavity.

For the structure using ultrasound, it is preferable that a scope-identifying unit for identifying a connected endoscopy scope be further included and that the distance-measuring unit store the calibration data set for each of at least one endoscopy scope.

The calibration data differs for each endoscopy scope. The distance-measuring unit stores calibration data for each endoscopy scope to be used. Since the scope-identifying unit identifies the connected endoscopy scope, the distance-measuring unit performs distance measurement with the calibration data for the identified endoscopy scope.

Thus, an appropriate one from among a plurality of endoscopy scopes can be selected according to the application and the purpose.

In the first and second aspects of the present invention, it is preferable that an angle-calculating unit for calculating an angle of the endoscopy scope relative to the tissue be further included.

As described above, since the angle-calculating unit for calculating the angle of the endoscopy scope relative to the tissue is provided, the fluorescence signal or the fluorescence image signal is corrected with the angle signal calculated by the angle-calculating unit to produce an image not affected by tilting of the endoscopy scope. Since an image of the tissue not affected by conditions of the endoscopy scope can be acquired, more accurate measurement is achieved.

For the structure for measuring the angle, it is preferable that the angle-calculating unit use ultrasound.

For the structure for measuring the angle, it is preferable that the angle-calculating unit use microwaves.

For the structure for measuring the angle, it is preferable that the angle-calculating unit use light.

For the structure using light, it is preferable that the light be a laser beam.

Since the angle can be measured in a non-contact manner, safety is increased when the endoscope apparatus is used in a body cavity.

In the first aspect of the present invention, it is preferable that the characteristic-value calculating unit include a post-administration-time correcting unit for correcting the fluorescence signal or the fluorescence image signal based on a time elapsed after administration of a fluorescence agent.

As described above, measurement can be started even before the administered fluorescence agent becomes sufficiently effective in the tissue because the measurement is corrected to a value as measured when the agent is sufficiently circulated through the tissue. This is advantageous in making a quicker diagnosis. Furthermore, the diagnostic accuracy is improved.

In the first and second aspects of the present invention, it is preferable that a light-source-intensity-fluctuation correcting unit for correcting the fluorescence signal or the fluorescence image signal based on a light intensity of the light source emitting the excitation light be further included.

Even if the light intensity of the light source fluctuates, causing, for example, the amount of fluorescence to change, the fluorescence signal or the fluorescence image signal is corrected with the light intensity of the light source. This eliminates adverse effects of fluctuation in light intensity of the light source. As a result, the accuracy for measuring fluorescence is increased and the diagnostic accuracy can be improved.

In the first aspect of the present invention, it is preferable that display be performed with different visual effects depending on the characteristic value calculated by the characteristic-value calculating unit.

With this approach, regions with high characteristic values can be easily differentiated from regions with low characteristic values. This allows the lesion to be diagnosed more effectively.

DETAILED DESCRIPTION OF THE INVENTION

Embodiments according to the present invention will now be described with reference to the drawings.

First Embodiment

An endoscope apparatus according to a first embodiment of the present invention will be described with reference to FIGS. 1 to 3.

In this embodiment, fluorochrome is used as a chemical agent.

Typical fluorochrome includes 5-ALA and indocyanine-green-derivative-labeled antibodies.

The characteristic that absorption and discharge speeds of 5-ALA have a greater difference in tumor cells than in normal cells is exploited. Based on this characteristic, fluorescence is measured when a gray level difference occurs between normal cells and tumor cells to identify a lesion.

Indocyanine-green-derivative-labeled antibodies couple with target molecules existing in cells or on cell surfaces. If a substance existing in cancer cells in abundance is set as a target molecule, indocyanine-green-derivative-labeled antibodies exhibit more affinity with a lesion containing cancer cells and accordingly build up more in the lesion, thus allowing the lesion to be identified.

With this mechanism, early cancer, which is difficult to detect through standard endoscopic examination, can be detected.

Figure 1:
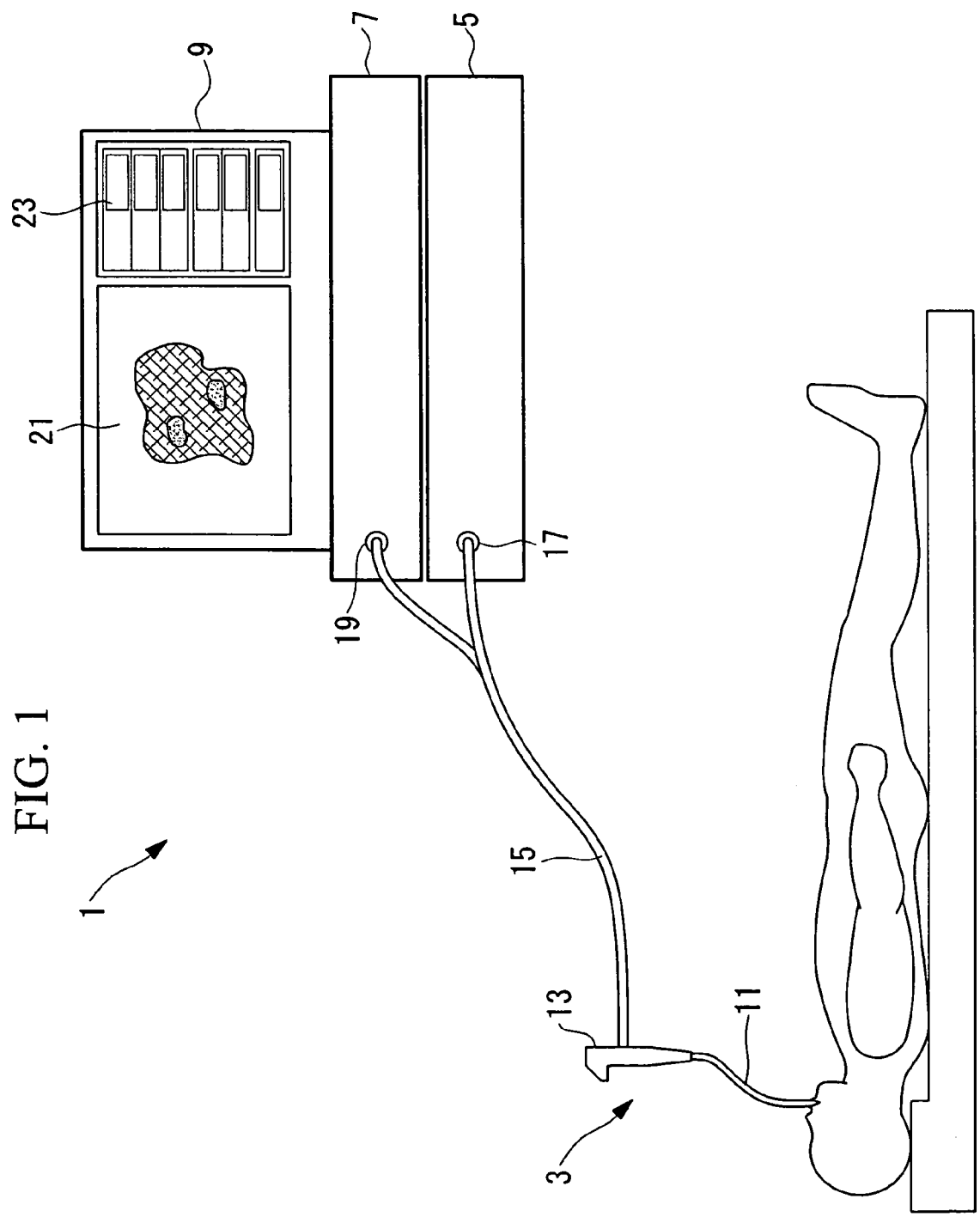
FIG. 1 is a diagram depicting the overall schematic structure of an endoscope apparatus according to a first embodiment of the present invention.

FIG. 1 is a diagram depicting the overall outline structure of an endoscope apparatus 1 according to this embodiment.

Referring to FIG. 1, the endoscope apparatus 1 includes an endoscopy scope 3 to be inserted into a body cavity or the lumen of an organ, a light source unit 5 for emitting illumination light and excitation light which are guided to the endoscopy scope 3, an image processor 7 for subjecting reflected light and fluorescence obtained through the endoscopy scope 3 to signal processing, and a monitor 9 for displaying an endoscopic image and a fluorescence image subjected to signal processing by the image processor 7.

The endoscopy scope 3 includes an insertion section 11 to be inserted into a body cavity or the lumen of an organ, an operating section 13 provided at the base end of the insertion section 11, and a universal cable 15 extending from the operating section 13. The universal cable 15 is divided into two sub-cables at an end away from the base end. The two sub-cables have connectors 17 and 19 at ends thereof, which are connected to the light source unit 5 and the image processor 7, respectively.

The monitor 9 includes a screen 21 for displaying images and a display section 23 for displaying characteristic values.

Figure 3:
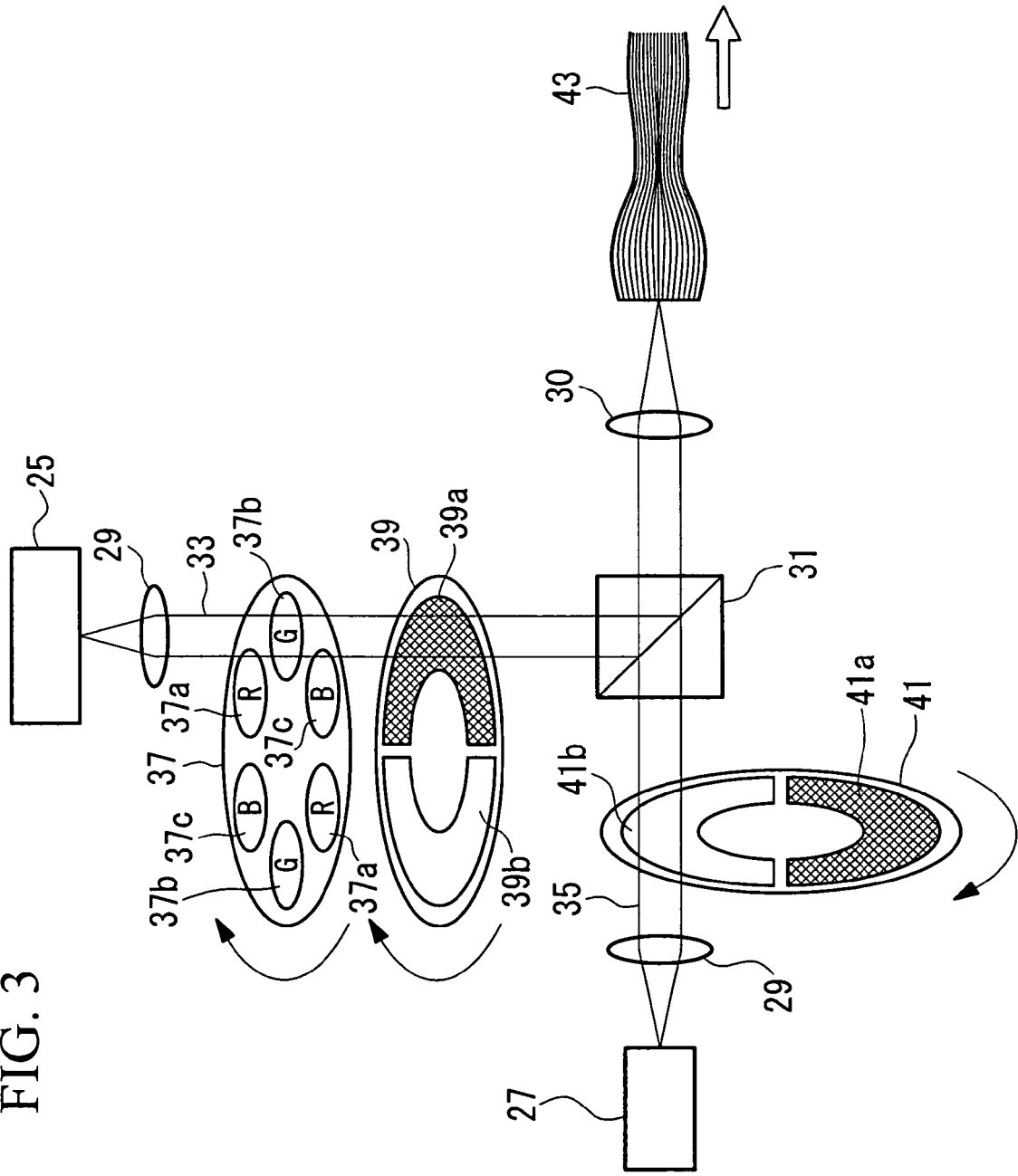
FIG. 3 is a diagram depicting the structure of a light source unit according to the first embodiment of the present invention.

FIG. 3 is a diagram depicting the structure of the light source unit 5.

The light source unit 5 includes a white light source 25 for generating illumination light, a laser light source 27 for generating excitation light, two collimator lenses 29, and a dichroic mirror 31.

The white light source 25 may be realized by, for example, a xenon lamp. The laser light source 27 may be realized by, for example, a semiconductor laser with a wavelength of 675 nm.

A white light path 33 extending from the white light source 25 is perpendicular to a laser light path 35 extending from the laser light source 27, and the dichroic mirror 31 is arranged at the intersection between the white light path 33 and the laser light path 35.

The dichroic mirror 31 transmits light with wavelengths in the vicinity of 675 nm, while reflecting light with other wavelengths.

Upstream of the dichroic mirror 31 along the white light path 33 are provided an RGB filter 37 and an ON/OFF filter 39, in that order from the upstream side to the downstream side.

The RGB filter 37 rotates about an axis parallel to the optical axis of the white light path 33. In a peripheral area of the RGB filter 37 through which the white light path 33 passes, two R filters 37a, two G filters 37b, and two B filters 37c for transmitting R (red), G (green), and B (blue) spectral-band light, respectively, are provided in the circumferential direction.

The ON/OFF filter 39 rotates about an axis parallel to the optical axis of the white light path 33. In a peripheral area of the ON/OFF filter 39 through which the white light path 33 passes, a light-blocking section 39a for blocking light and a light-transmitting section 39b for transmitting light are provided in the circumferential direction such that the ON/OFF filter 39 is equally separated into the light-blocking section 39a and the light-transmitting section 39b.

Another ON/OFF filter 41 is provided upstream of the dichroic mirror 31 along the laser light path 35.

The ON/OFF filter 41 rotates about an axis parallel to the optical axis of the laser light path 35. In a peripheral area of the ON/OFF filter 41 through which the white light path 35 passes, a light-blocking section 41a for blocking light and a light-transmitting section 41b for transmitting light are provided in the circumferential direction such that the ON/OFF filter 41 is equally separated into the light-blocking section 41a and the light-transmitting section 41b.

The ON/OFF filter 39 and the ON/OFF filter 41 are controlled to rotate such that the light-transmitting section 41b of the ON/OFF filter 41 is located on the laser light path 35 while the light-blocking section 39a of the ON/OFF filter 39 blocks light along the white light path 33. In other words, illumination light from the white light source 25 and excitation light from the laser light source 27 are alternately incident on the dichroic mirror 31.

Illumination light emitted from the white light source 25 is converted into collimated light by one collimator lens 29 and is split into light of red, green, and blue wavelength ranges by the RGB filter 37. Thereafter, the light is reflected at the dichroic mirror 31 and focused onto one end of an illumination fiber bundle 43 (to be described later) through an exit-side collimator lens 30.

On the other hand, excitation light emitted from the laser light source 27 is converted into collimated light through the other collimator lens 29, passes through the dichroic mirror 31, and is focused onto one end of the illumination fiber bundle 43 (to be described later) through the exit-side collimator lens 30.

Figure 2:
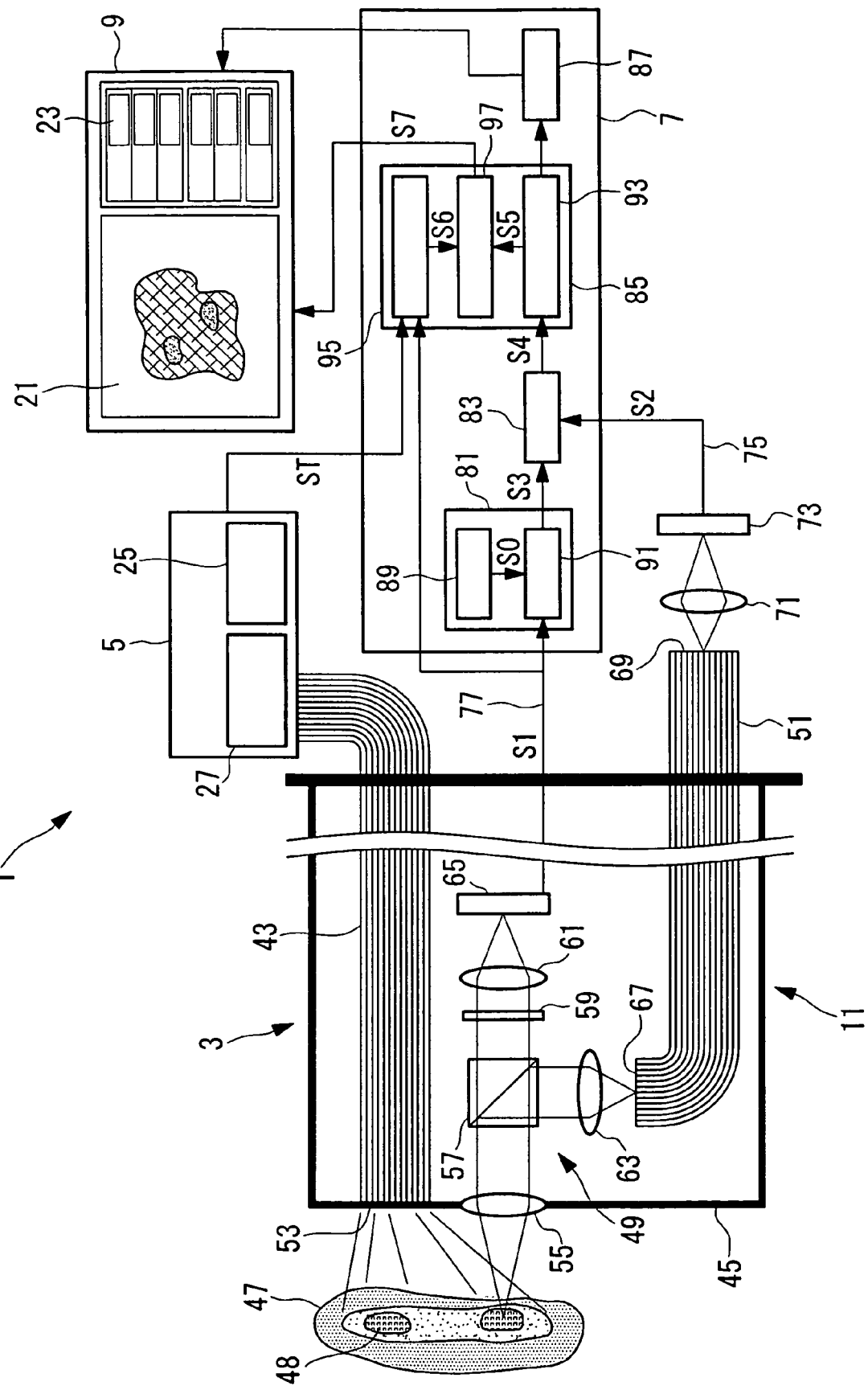
FIG. 2 is a block diagram depicting the overall structure of the endoscope apparatus according to the first embodiment of the present invention.

FIG. 2 is a block diagram depicting the overall structure of the endoscope apparatus 1. Components other than the light source unit 5 will be described with reference to FIG. 2.

The endoscopy scope 3 includes the illumination fiber bundle 43 for transmitting illumination light and excitation light from the light source unit 5; an objective optical system 49 disposed at an end portion 45 of the insertion section 11 to receive reflected light from a tissue 47; and a fluorescence fiber bundle 51 for transmitting fluorescence separated by the objective optical system 49.

The illumination fiber bundle 43 extends from the light source unit 5, via the connector 17 and the universal cable 15, to the insertion section 11. It transmits illumination light and excitation light emitted from the light source unit 5 and irradiates the illumination light and excitation light externally through an irradiation section 53 formed at the end portion 45 of the insertion section 11. This illumination fiber bundle 43 is made of, for example, multicomponent glass fiber or quartz fiber.

The objective optical system 49 includes an objective lens 55, a fluorescence filter 57 for separating fluorescence excited by the excitation light from normal reflected light, a barrier filter 59, a reflected-light focusing lens 61, and a fluorescence focusing lens 63. The wavelength of fluorescence excited by excitation light with a wavelength of 675 nm is 690 nm.

The objective lens 55 is disposed at the end portion 45 of the insertion section 11, and receives reflected light and fluorescence from the tissue 47 to convert it into collimated light.

The fluorescence filter 57 is an optical element that separates light coming through the objective lens 55 into fluorescence and reflected light by reflecting light in the fluorescence band (light with a wavelength of 690 nm and its neighboring wavelengths) at a right angle, while transmitting light with other wavelengths.

The barrier filter 59 is disposed downstream of the fluorescence filter 57 on the incident light axis of the fluorescence filter 57, and cuts off excitation light with a wavelength of 675 nm.

To cut off excitation light included in the reflected light, an ON/OFF filter with the same structure as that of the ON/OFF filter 39 may be arranged in place of the barrier filter 59 so as to block and transmit light with the same timing as the ON/OFF filter 39.

The reflected-light focusing lens 61 is disposed downstream of the barrier filter 59 and focuses reflected light passing through the fluorescence filter 57 and the barrier filter 59 onto a CCD (reflected-light imaging unit) 65.

In the CCD 65, the reflected light focused onto the imaging surface is converted into an electrical signal, which is referred to as a reflected-light signal S1. The reflected-light signal S1 is transmitted to the image processor 7 via a signal cable 77.

The fluorescence focusing lens 63 is arranged in a direction perpendicular to the incident light axis of the fluorescence filter 57 to focus fluorescence reflected by the fluorescence filter 57 onto one end 67 of the fluorescence fiber bundle 51.

The fluorescence transmitted to the other end 69 of the fluorescence fiber bundle 51 is focused, via a lens 71, onto a CCD 73 incorporating an imaging intensifier. A cooled CCD with reduced thermal noise may be used instead of the CCD 73 incorporating an imaging intensifier.

In the CCD 73 incorporating an imaging intensifier, weak fluorescence is amplified into an electrical signal, which is referred to as a fluorescence signal S2. The fluorescence signal S2 is transmitted to the image processor 7 via a signal cable 75.

The image processor 7 includes a distance-measuring unit 81, an amount-of-fluorescence calculating unit (characteristic-value calculating unit) 83, an image-processing unit 85, and an amount-calculating unit 87.

The distance-measuring unit 81 includes a reference-value setting unit 89 for setting a reflected-light intensity signal S0 when the end portion 45 of the endoscopy scope 3 is a predetermined distance away from the tissue 47 and a distance-computing unit 91. The distance-computing unit 91 produces a distance signal S3 by dividing the reflected-light intensity signal S0 set in the reference-value setting unit 89 at the predetermined distance by the mean value of the measured reflected-light signal S1, which is transmitted via the signal cable 77.

The relationship of the measured intensity, i.e., the amount of reflected light with the distance between the end portion 45 and the tissue 47 is similar inversely proportional relationship. Therefore, when the distance at the time of measurement is, for example, shorter than the predetermined distance, the reflected-light signal S1 indicating the measured intensity of the reflected light has a higher intensity than the intensity signal S0 set at the predetermined distance. Thus, the distance signal S3 computed in the distance-computing unit 91 is smaller than 1, indicating that the distance at the time of measurement is shorter than the predetermined distance.

The amount-of-fluorescence calculating unit 83 produces a corrected fluorescence signal S4 by multiplying the distance signal S3 by the fluorescence signal S2 transmitted via the signal cable 75.

The relationship of the measured fluorescence intensity (the amount of fluorescence) with the distance between the end portion 45 and the tissue 47 is similar inversely proportional relationship. Therefore, when the distance at the time of measurement is, for example, shorter than the predetermined distance, the fluorescence signal S2 has a value larger than the actual value. The corrected fluorescence signal S4 is a signal corrected for short distance because it is produced by multiplying this fluorescence signal S2 having a larger value by the distance signal S3 having a value smaller than 1.

In contrast, when the distance at the time of measurement is longer than the predetermined distance, the corrected fluorescence signal S4 is corrected to have a larger value than the measured fluorescence signal S2.

In other words, the corrected fluorescence signal S4 is corrected to indicate the actual amount of fluorescence by appropriately setting the reflected-light intensity signal S0, regardless of whether the distance between the end portion 45 of the endoscopy scope 3 and the tissue 47 is shorter or longer than the predetermined distance.

The image-processing unit 85 includes a fluorescence-image generating unit 93, an endoscopic-image generating unit 95, and a superimposer (image superimposing unit) 97.

The fluorescence-image generating unit 93 produces a fluorescence image signal S5 based on the corrected fluorescence signal S4 from the amount-of-fluorescence calculating unit 83.

The endoscopic-image generating unit 95 produces an endoscopic image signal S6 based on the reflected-light signal S1 with a timing according to a trigger signal ST from the light source unit 5.

The fluorescence image signal S5 and the endoscopic image signal S6 are input to the superimposer 97. The superimposer 97 produces a superimposed-image signal S7 including, for example, one image serving as a main image and another serving as a sub-image superimposed on the main image.

The superimposed-image signal S7 generated by the superimposer 97 is output to the monitor 9 to display a composite image on the screen 21.

Images to be displayed on the monitor 9 are not limited to the above-described composite image. Instead, only one of the main and sub-images may be displayed on the monitor 9. Commands for switching between the main image and the sub-image and for displaying only one of the main and sub-images can be issued using a switch (not shown) provided in the image processor 7.

Furthermore, in the amount-calculating unit 87, the amounts of target substances are calculated based on the amount of fluorescence from the fluorescence image signal S5, and these calculated values are displayed in the display section 23 of the monitor 9.

The operation of the endoscope apparatus 1, according to this embodiment, with the above-described structure will now be described.

First, fluorochrome, such as 5-ALA or indocyanine-green-derivative-labeled antibodies, is administered to the tissue 47. Diagnosis is started with the endoscope apparatus 1 a predetermined period of time after the administration.

The fluorochrome, such as 5-ALA or indocyanine-green-derivative-labeled antibodies, is accumulated more in cancer cells of a lesion 48 than in normal cells, thus emitting fluorescence.

When the light-transmitting section 39b of the ON/OFF filter 39 is located on the white light path 33, the endoscope apparatus 1 operates as follows. Illumination light emitted from the white light source 25 is converted into collimated light by the collimator lens 29 and is incident upon the RGB filter 37. The white light path 33 sequentially passes through the R filter 39a, the G filter 39b, and the B filter 39c as the RGB filter 37 rotates to split the illumination light into light of red, green, and blue wavelength ranges. This split light is then reflected at the dichroic mirror 31 and focused onto one end of the illumination fiber bundle 43 through the exit-side collimator lens 30.

This focused light is transmitted through the illumination fiber bundle 43 and is irradiated onto the tissue 47 from the irradiation section 53 provided at the end portion 45.

Reflected light from the tissue 47 is converted into collimated light by the objective lens 55, passes through the fluorescence filter 57, and is focused on the CCD 65 by the focusing lens 61. In the CCD 65, the reflected light focused onto the imaging surface is converted into an electrical signal, which forms the reflected-light signal S1. The reflected-light signal S1 is transmitted to the distance-computing unit 91 and the endoscopic-image generating unit 95 via the signal cable 77.

In the endoscopic-image generating unit 95, the endoscopic image signal S6 is generated from the reflected-light signal S1. According to this endoscopic image signal S6, the illumination light is wideband light with a visible-light range roughly divided into three wavelength ranges of blue, green, and red. This illumination light allows a bright color image to be produced with good color reproducibility.

On the other hand, when the light-transmitting section 41b of the ON/OFF filter 41 is located on the laser light path 35, excitation light emitted from the laser light source 27 is converted into collimated light by the collimator lens 29, passes through the dichroic mirror 31, and is focused onto one end of the illumination fiber bundle 43 by the exit-side collimator lens 30. This focused excitation light is transmitted via the illumination fiber bundle 43 and is irradiated onto the tissue 47 from the irradiation section 53 provided at the end portion 45.

As a result of this excitation light being irradiated, fluorochrome, such as 5-ALA or indocyanine-green-derivative-labeled antibodies, accumulated in cancer cells is excited to emit fluorescence. This fluorescence is converted into collimated light through the objective lens 55, is reflected at the fluorescence filter 57, and is focused onto one end 67 of the fluorescence fiber bundle 51 by the focusing lens 63.

This focused fluorescence is transmitted via the fluorescence fiber bundle 51 and the other end 69 and is focused onto the CCD 73 incorporating an imaging intensifier by the lens 71. In the CCD 73 incorporating an imaging intensifier, weak fluorescence is amplified into an electrical signal, which is the fluorescence signal S2. The fluorescence signal S2 is transmitted to the amount-of-fluorescence calculating unit 83 via the signal cable 75.

The above-described series of operations for illumination light and excitation light are performed alternately according to the operating timing of the ON/OFF filters 39 and 41.

The distance-computing unit 91 receives the reflected-light signal S1 and the reflected-light intensity signal S0 set at the predetermined distance stored in the reference-value setting unit 89 via the signal cable 77. In the distance-computing unit 91, the intensity signal S0 is divided by the calculated mean value of the reflected signal S1 to output the distance signal S3. The distance signal S3 is indicated in the form of a ratio of the distance at the time of measurement to the predetermined distance.

As described above, merely setting the reflected light intensity S0 at the predetermined distance allows the distance signal S3 corresponding to the distance between the irradiation section 53 and the tissue 47 to be obtained based on the reflected-light signal S1 indicating the intensity of reflected light from the tissue 47. This is advantageous in that no devices for distance measurement are required. Therefore, the structure of the endoscopy scope 3 can be simplified, and the endoscopy scope 3 can thus be manufactured at low cost.

The distance signal S3 is transmitted to the amount-of-fluorescence calculating unit 83, where the distance signal S3 is multiplied by the fluorescence signal S2 transmitted via the signal cable 75 to output the corrected fluorescence signal S4. This means that the fluorescence signal S2 is corrected using the distance signal S3 to form the corrected fluorescence signal S4 since reflected light and fluorescence, both being light, have substantially the same attenuation factors according to distance.

Although the distance signal S3 is generated based on reflected light in this embodiment, the present invention is not limited to this approach. For example, the distance signal S3 may be generated based on the fluorescence signal S2 by setting the fluorescence intensity at the predetermined distance.

The corrected fluorescence signal S4 is transmitted to the fluorescence-image generating unit 93. The fluorescence-image generating unit 93 generates the fluorescence image signal S5 from the corrected fluorescence signal S4.

The fluorescence image signal S5 and the endoscopic image signal S6 are input to the superimposer 97. The superimposer 97 produces the superimposed-image signal S7 including, for example, one image serving as a main image and another serving as a sub-image superimposed on the main image.

The superimposed-image signal S7 generated by the superimposer 97 is output to the monitor 9, where the composite image is displayed on the screen 21.

As described above, according to this embodiment, the fluorescence signal S2 indicating the amount of fluorescence is corrected with the distance signal S3, and thereby the corrected fluorescence signal S4 not influenced by the distance between the irradiation section 53 and the tissue 47 is generated. Since a fluorescence image is displayed on the monitor 9 based on this corrected fluorescence signal S4, the amount of fluorescence not influenced by the distance between the irradiation section 53 and the tissue 47 is displayed on the monitor 9. As described above, since a distance-independent amount of fluorescence is displayed on the monitor 9, quantitative diagnosis of a lesion can be made for increased diagnostic accuracy.

Furthermore, according to this embodiment, since the superimposer 97 combines the endoscopic image signal S6 and the fluorescence image signal S5, a fluorescence image showing, for example, a lesion can be superimposed on an endoscopic image showing a normal external view. Because of this, the region in the tissue 47 where a lesion exists can be displayed in association with the external view. This allows the lesion to be located correctly.

In addition, since the fluorescence image shows the amount of fluorescence which is not influenced by the distance between the irradiation section 53 and the tissue 47, quantitative diagnosis of the lesion can be made for increased diagnostic accuracy.

When the fluorescence image signal S5 is to be displayed on the screen 21 of the monitor 9, it is preferable that different visual effects be used depending on whether the fluorescence intensity is high or low.

Different visual effects include display in different color tones, display in different colors, and display with different blink rates.

With these different visual effects, a site with high fluorescence intensity, i.e., a site including more cancer cells, can be identified easily. This allows, for example, the danger of cancer metastasis or the stage of cancer progression to be evaluated based on the fluorescence image on the monitor 9.

Furthermore, the amount-calculating unit 87 can calculate the amounts of target substances based on the amount of fluorescence from the fluorescence image signal S5 to display these values in the display section 23 of the monitor 9.

In addition, information such as the amount of fluorescence and the size of the cancer may be additionally displayed.

With these additional items of information, for example, the size of the cancer can be indicated numerically. This increases the diagnostic accuracy.

Figure 4:
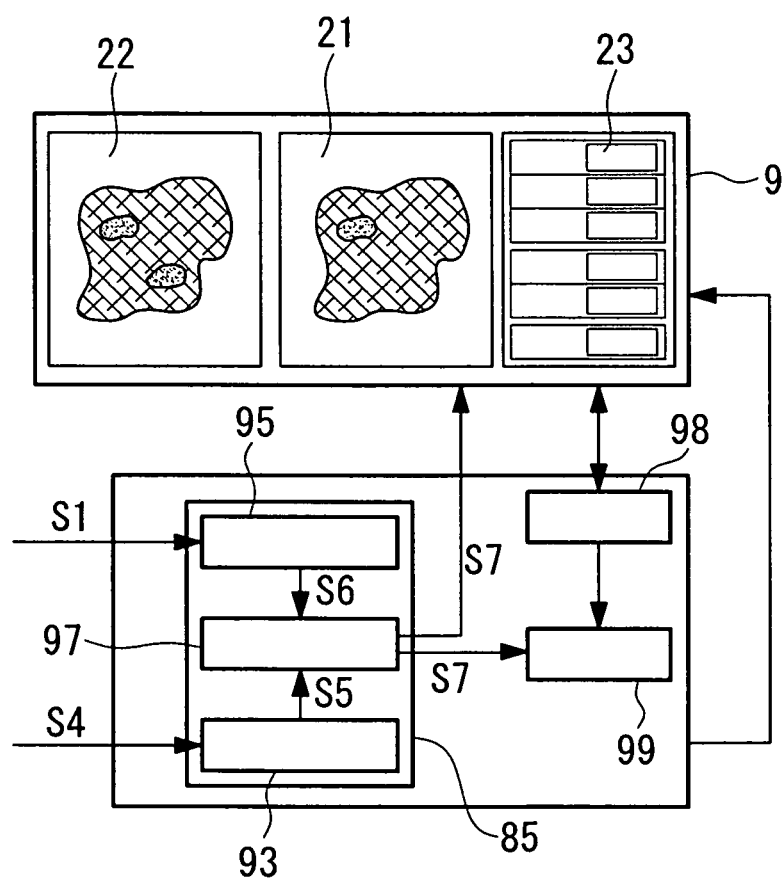
FIG. 4 is a block diagram depicting another example of an image processor according to the first embodiment of the present invention.

The image processor 7 according to this embodiment may be additionally provided with an image-storing unit 98 and an image-matching unit 99, as shown in FIG. 4.

In FIG. 4, an additional screen 22 is provided next to the screen 21 on the monitor 9.

The image-storing unit 98 stores necessary superimposed-image signals S7. The necessary superimposed-image signals S7 are, for example, signals of images showing sites including possible lesions.

The image-matching unit 99 matches the superimposed-image signal S7 currently being generated by the superimposer 97 against one superimposed-image signal (referred to as a previous superimposed-image signal) S8 selected from among the superimposed-image signals S7 saved in the image-storing unit 98 by means of feature extraction using the endoscopic image signal S6 with less change in shape.

The previous superimposed-image signal S8 is transmitted from the image-storing unit 98 to the image-matching unit 99 and the monitor 9 and is displayed on the screen 22 of the monitor 9. The superimposed-image signal S7 is transmitted from the superimposer 97 to the image-matching unit 99 and the monitor 9 and is displayed on the screen 21 of the monitor 9.

In the image-matching unit 99, the previous superimposed-image signal S8 is sequentially matched against the continuously changing superimposed-image signal S7. When matching is achieved, the operator is informed with appropriate information such as audio output or a lamp.

With the above-described structure, the sites stored in the image-storing unit 98 can easily be reproduced. Therefore, even if, for example, the endoscopy scope 3 is undesirably moved or fluorescence from the chemical agent fades during fluoroscopy, the state before such an incident occurs can be restored immediately to continue fluoroscopy. Furthermore, the pre- and post-operative states of a site can be compared on the monitor 9 to evaluate the therapeutic effect, for example.

Second Embodiment

A second embodiment of the present invention will be described with reference to FIGS. 5 to 7.

The basic structure of the endoscope apparatus 1 according to this embodiment is the same as that of the endoscope apparatus 1 according to the first embodiment, except for the structure of the distance-measuring unit and the mechanism for generating the fluorescence image signal.

The description below mainly focuses on these differences.

The same components in this embodiment as those used in the first embodiment are denoted by the same reference numerals, and thus will not be described.

Figure 5:
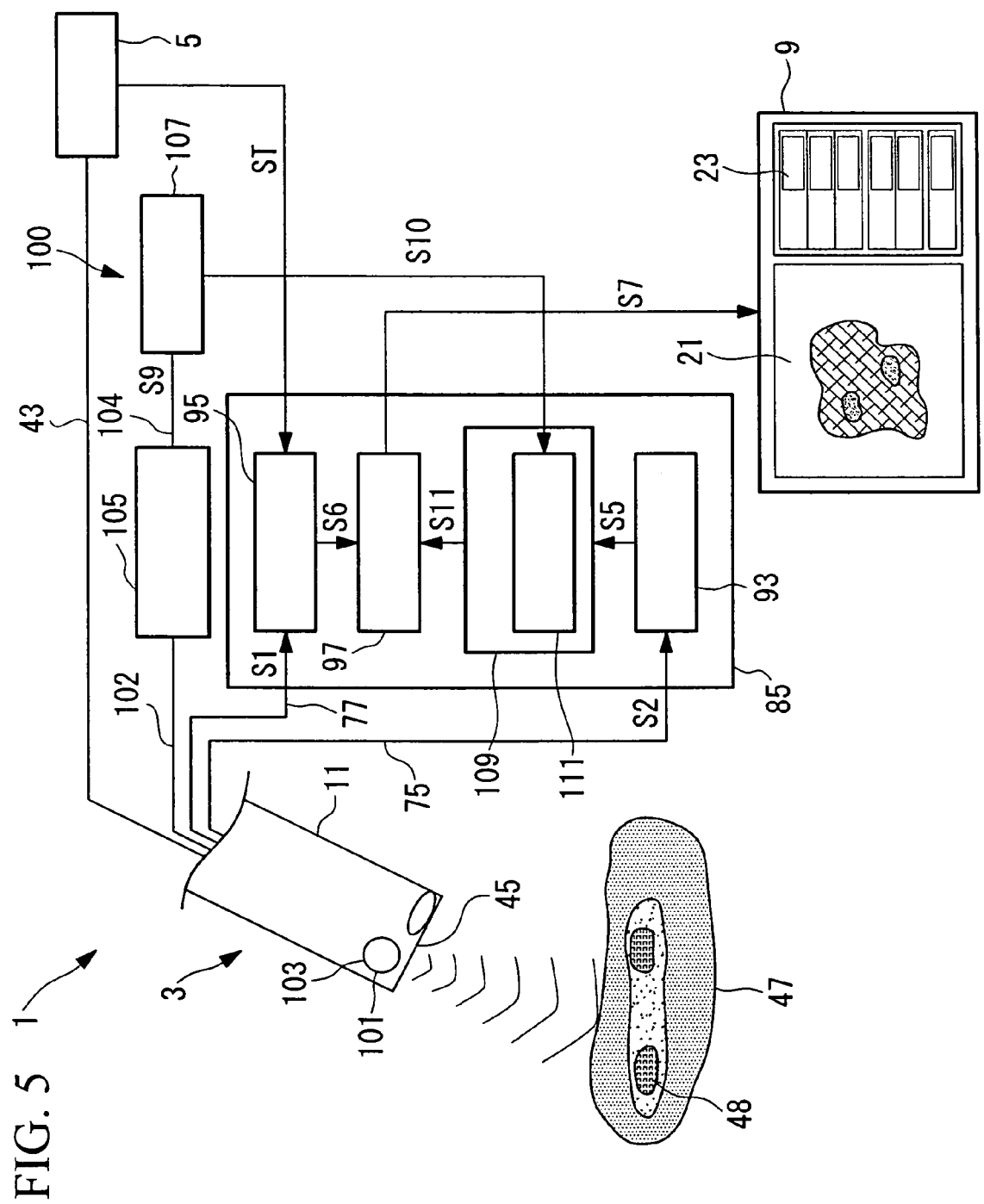
FIG. 5 is a block diagram depicting the overall structure of an endoscope apparatus according to a second embodiment of the present invention.

FIG. 5 is a block diagram depicting the overall outline structure of the endoscope apparatus 1 according to this embodiment. FIG. 7 is a diagram depicting the light source unit 5 to which the endoscopy scope 3 is connected.

A distance-measuring unit 100 of the endoscope apparatus 1 according to this embodiment will be described. The distance-measuring unit 100 includes an ultrasound generator 101 and an ultrasound detector 103 provided at the end portion 45 of the insertion section 11 of the endoscopy scope 3, an ultrasound-signal processing unit 105 provided in the light source unit 5, and a distance-computing unit 107.

The ultrasound generator 101 and the ultrasound detector 103 are connected to the ultrasound-signal processing unit 105 with a signal cable 102 extending through the insertion section 11 and the universal cable 15. The signal cable 102 connects the ultrasound generator 101 and the ultrasound detector 103 to the ultrasound-signal processing unit 105 when the connector 17 of the endoscopy scope 3 is inserted into the light source unit 5. The ultrasound-signal processing unit 105 is connected to the distance-computing unit 107 with a signal cable 104.

The ultrasound-signal processing unit 105 not only controls transmission/reception of ultrasound by the ultrasound generator 101 and the ultrasound detector 103, but outputs a detector output signal S9 detected by the ultrasound detector 103 to the distance-computing unit 107.

The detector output signal S9 is a signal having a value proportional to, for example, the intensity of detected ultrasound or the time from when ultrasound is emitted to when an ultrasound echo is received.

Figure 6:
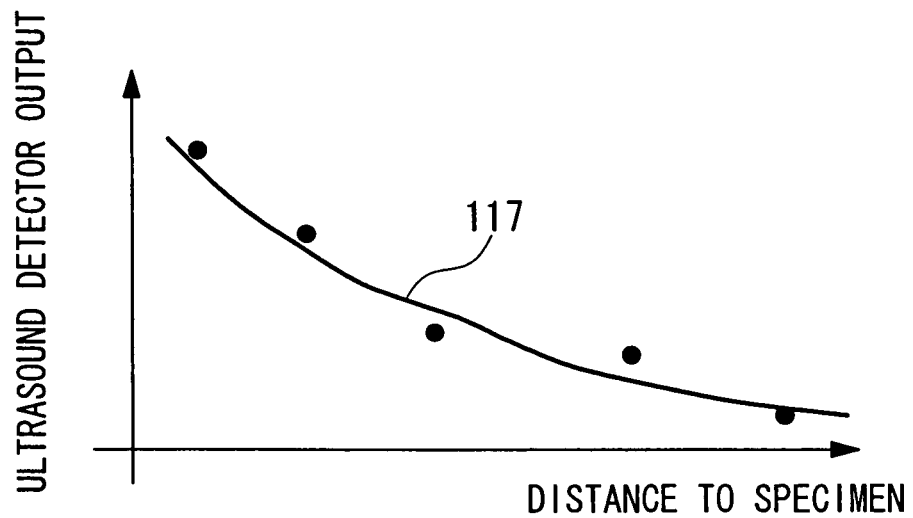
FIG. 6 shows calibration data according to the second embodiment of the present invention.
Figure 7:
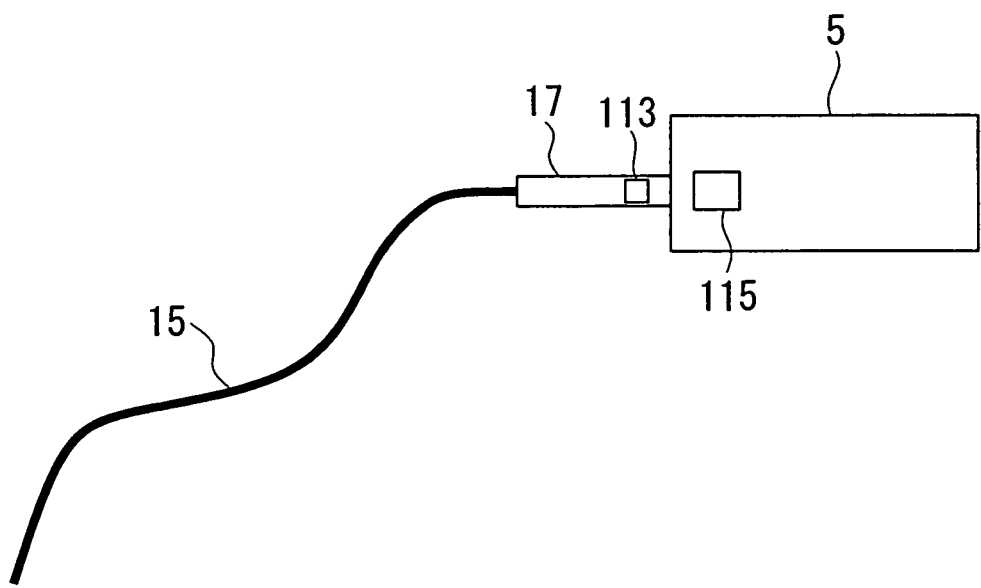
FIG. 7 is a diagram depicting the structure of a light source unit according to the second embodiment of the present invention.

The distance-computing unit 107 includes calibration data 117, as shown in FIG. 6, indicating the relationship between the distance to the tissue 47 and the ultrasound detector output. Based on this calibration data 117, the distance between the end portion 45 and the tissue 47 is calculated through the use of the detector output signal S9 from the ultrasound-signal processing unit 105 to output a distance signal S10. The calibration data 117 shown in FIG. 6 is data plotted based on the relationships between various distances and corresponding detector outputs, pre-measured with the endoscopy scope 3.

Since the calibration data 117 differs for each endoscopy scope 3, the distance-computing unit 107 stores all calibration data 117 associated with a plurality of endoscopy scopes 3 to be used with the endoscope apparatus 1. Each endoscopy scope 3 has, in the connector 17, an IC chip 113 storing data to identify the endoscopy scope 3 itself. The light source unit 5 includes a reading section (scope-identifying unit) 115 for reading out the data in this IC chip 113 to identify the calibration data 117 to be used.

The second embodiment differs from the first embodiment in that the image-processing unit 85 includes an amount-of-fluorescence calculating unit 109 between the fluorescence-image generating unit 93 and the superimposer 97 and that the fluorescence signal S2 is input directly to the fluorescence-image generating unit 93.

In the fluorescence-image generating unit 93, the fluorescence image signal S5 is generated from the input fluorescence signal S2 and output to the amount-of-fluorescence calculating unit 109.

The amount-of-fluorescence calculating unit 109 includes a distance-correcting unit 111. The distance-correcting unit 111 corrects the fluorescence image signal S5 with the distance signal S10 from the distance-computing unit 107 to generate a corrected fluorescence-image signal S11.

The corrected fluorescence-image signal S11 is transmitted to the superimposer 97.

The operation of the endoscope apparatus 1 with the above-described structure according to this embodiment will be described.

Administration of a chemical agent, irradiation of illumination light and excitation light, detection of reflected light and fluorescence, generation of the reflected-light signal S1 and the fluorescence signal S2, as well as display on the monitor 9 according to this embodiment are the same as those according to the first embodiment, and thus will not be described below.

When the connector 17 of the endoscopy scope 3 to be used for examination is connected to the light source unit 5, the reading section 115 reads out data stored in the IC chip 113 mounted on the connector 17 and selects the calibration data 117 corresponding to the read out data.

Under the control of the ultrasound-signal processing unit 105, the ultrasound generator 101 irradiates an ultrasound signal onto the tissue 47. The ultrasound detector 103 detects an ultrasound signal reflected at the tissue 47, converts it into the detector output signal S9, and transmits it to the ultrasound-signal processing unit 105.

The detector output signal S9 is transmitted from the ultrasound-signal processing unit 105 to the distance-computing unit 107. In the distance-computing unit 107, the distance from the end portion 45 to the tissue 47 is calculated from this detector output signal S9 based on the selected calibration data 117 to output the result as the distance signal S10.

In the fluorescence-image generating unit 93, the fluorescence image signal S5 is generated from the fluorescence signal S2 and transmitted to the amount-of-fluorescence calculating unit 109.

In the amount-of-fluorescence calculating unit 109, the distance-correcting unit 111 corrects the fluorescence image signal S5 with the distance signal S10 transmitted from the distance-computing unit 107 to generate the corrected fluorescence-image signal S11. The corrected fluorescence-image signal S11 is input to the superimposer 97, as well as the endoscopic image signal S6 generated in the endoscopic-image generating unit 95 to generate the superimposed-image signal S7.

The superimposed-image signal S7 generated by the superimposer 97 is output to the monitor 9 and a composite image is displayed on the screen 21.

As described above, according to this embodiment, the fluorescence image signal S5 generated from the fluorescence signal S2 indicating the amount of fluorescence is corrected with the distance signal S10 to generate the corrected fluorescence-image signal S11, which is not influenced by the distance to the tissue 47. Since a fluorescence image is displayed on the monitor 9 based on this corrected fluorescence-image signal S11, the amount of fluorescence not influenced by the distance between the irradiation section 53 and the tissue 47 is displayed on the monitor 9. Since the amount of fluorescence not influenced by the distance to the tissue 47 is indicated as described above, quantitative diagnosis of a lesion can be made for improved diagnostic accuracy.

Although in this embodiment the distance-measuring unit 100 exploits ultrasound for distance measurement, the present invention is not limited to this approach. For example, microwaves may be used instead of ultrasound for distance measurement.

More specifically, a microwave generator and an antenna for receiving reflected waves may be mounted at the end portion 45 on the insertion section 11 of the endoscopy scope 3, and the distance from the end portion 45 to the tissue 47 is obtained by measuring the time from when microwaves are emitted from the microwave generator to the tissue 47 to when reflected waves from the tissue 47 are received at the antenna.

In this manner, the distance from the end portion 45 to the tissue 47 can be measured more accurately because microwaves are attenuated less and have higher time resolution than ultrasound.

Instead of microwaves, light such as laser light may also be used for distance measurement.

Figure 10:
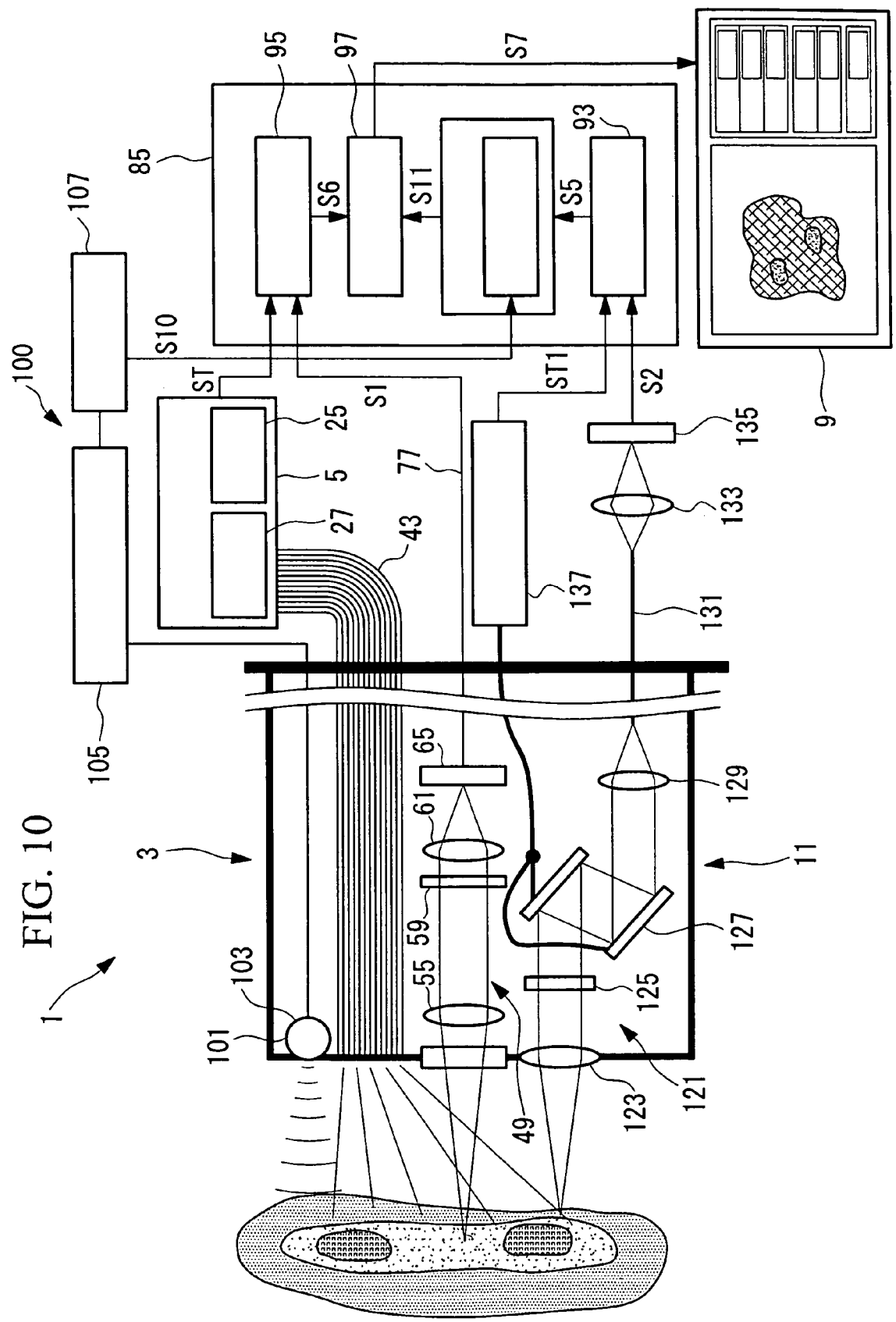
FIG. 10 is a block diagram depicting another example of the endoscope apparatus according to the first embodiment of the present invention.

Furthermore, although in this embodiment one objective optical system 49 is used to detect both reflected light and fluorescence (refer to FIG. 2 showing the endoscope apparatus 1 according to the first embodiment), different objective optical systems may be used to detect reflected light and fluorescence, as shown in FIG. 10.

More specifically, a fluorescence objective optical system 121 is employed in place of the fluorescence filter 57 and the focusing lens 63 of the objective optical system 49.

The fluorescence objective optical system 121 includes a fluorescence objective lens 123, an excitation-light cutting filter 125 for transmitting only fluorescence, a scanning mirror 127, a focusing lens 129, an optical fiber 131, a lens 133, a photomultiplier tube (PMT) 135, and a scanning-mirror driving unit 137 for driving the scanning mirror 127.

Fluorescence entering the fluorescence objective lens 123 passes through the excitation-light cutting filter 125, is scanned by the scanning mirror 127, and is focused onto one end of the optical fiber 131 through the focusing lens 129. The fluorescence that has passed through the optical fiber 131 exits from the other end of the optical fiber 131, is focused onto the photomultiplier tube 135 through the lens 133, and is converted into the fluorescence signal S2 by the photomultiplier tube 135.

Since the scanning mirror 127 is used to perform scanning as described above, a photodetector formed in an array, such as a CCD, is not necessary. In short, an expensive CCD incorporating an imaging intensifier is not required. For this reason, a relatively low-cost photomultiplier tube 135 can be used instead of an expensive CCD. This allows the endoscope apparatus 1 to be manufactured at low cost.

Third Embodiment

A third embodiment of the present invention will be described with reference to FIG. 8.

The structure of the endoscope apparatus 1 according to this embodiment is the same as that of the endoscope apparatus 1 according to the second embodiment, except for the structure of the image-processing unit 85.

The following description mainly focuses on this difference.

The same components in this embodiment as those used in the above-described embodiments are denoted by the same reference numerals, and thus will not be described.

Figure 8:
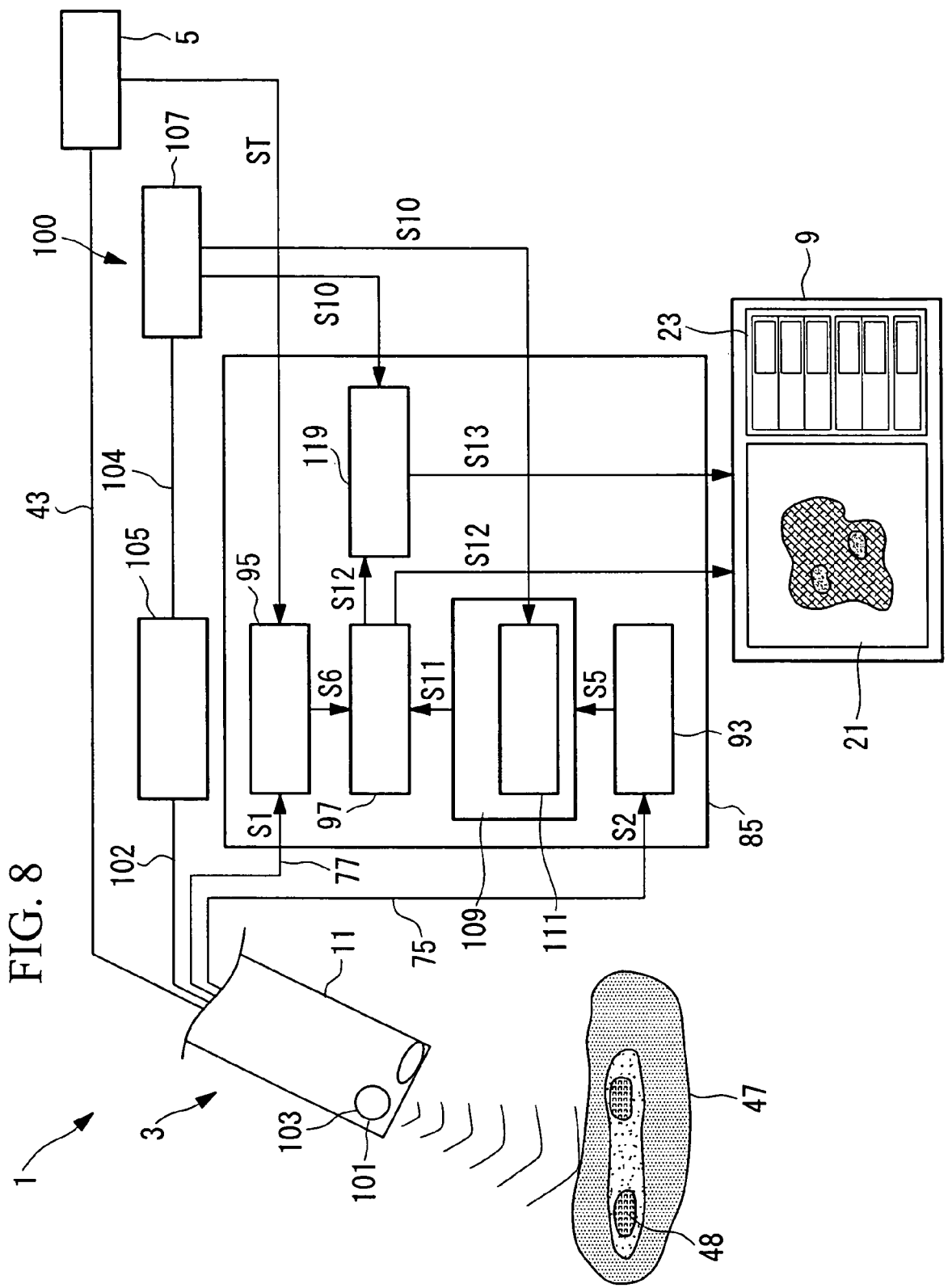
FIG. 8 is a block diagram depicting the overall structure of an endoscope apparatus according to a third embodiment of the present invention.

FIG. 8 is a block diagram depicting the overall outline structure of the endoscope apparatus 1 according to this embodiment.

The third embodiment differs from the second embodiment in that the image-processing unit 85 includes an image-size calculating unit 119 for calculating image sizes.

The image-size calculating unit 119 receives a superimposed-image signal S12 from the superimposer 97 and the distance signal S10 from the distance-computing unit 107.

The image-size calculating unit 119 calculates the image size of the superimposed-image signal S12 on a scale at the predetermined distance and corrects the calculated size into an actual size with the distance signal S10 to transmit the actual size to the monitor 9 as a size signal S13. The image size obtained in this manner is numerically displayed in the display section 23 of the monitor 9.

As described above, according to this embodiment, since the actual size of a composite image is displayed, the size of a fluorescence image can be obtained quantitatively. Therefore, the size of a region inducing substances generating fluorescence in a lesion such as cancer can be obtained quantitatively. This allows the extent of the lesion to be accurately diagnosed.

Although in this embodiment the image size of a composite image is numerically displayed in the section 23, the present invention is not limited to this approach.

Figure 9:
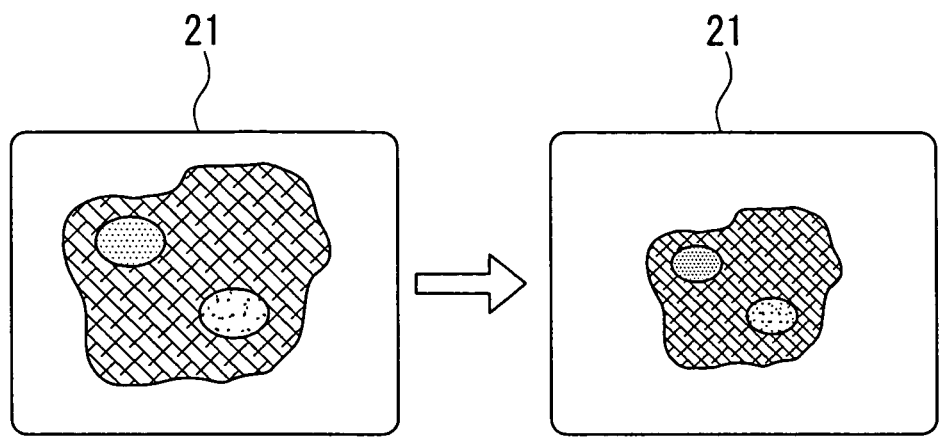
FIG. 9 is a front view of a screen according to the third embodiment of the present invention.

For example, in the image-size calculating unit 119, the superimposed-image signal S12 itself may be corrected on a scale obtained by correcting the scale of the predetermined distance using the distance signal S10. The superimposed-image signal S12 thus corrected may be transmitted to the monitor 9 and the screen display size of the monitor 9 may be corrected as shown in FIG. 9. Furthermore, the corrected scale may be displayed on the screen 21.

The left screen 21 in FIG. 9 shows an image appearing larger because the distance between the end portion 45 of the endoscopy scope 3 and the tissue 47 is shorter than the predetermined distance. The right screen 21 in FIG. 9 shows an image subjected to the above-described size correction, thus appearing smaller.

Furthermore, the numerical indication and correction of the screen display size according to the third embodiment may be combined.

This further improves the diagnostic accuracy.

Fourth Embodiment

A fourth embodiment of the present invention will be described with reference to FIG. 11.

The basic structure of the endoscope apparatus 1 according to this embodiment is the same as that of the endoscope apparatus 1 according to the second embodiment. The fourth embodiment differs from the second embodiment in the structure of the end portion of the insertion section 11, the mechanism for fluorescence detection, and the structure of the image-processing unit 85.

The description below mainly focuses on these differences.

The same components in this embodiment as those used in the above-described embodiments are denoted by the same reference numerals, and thus will not be described.

Figure 11:
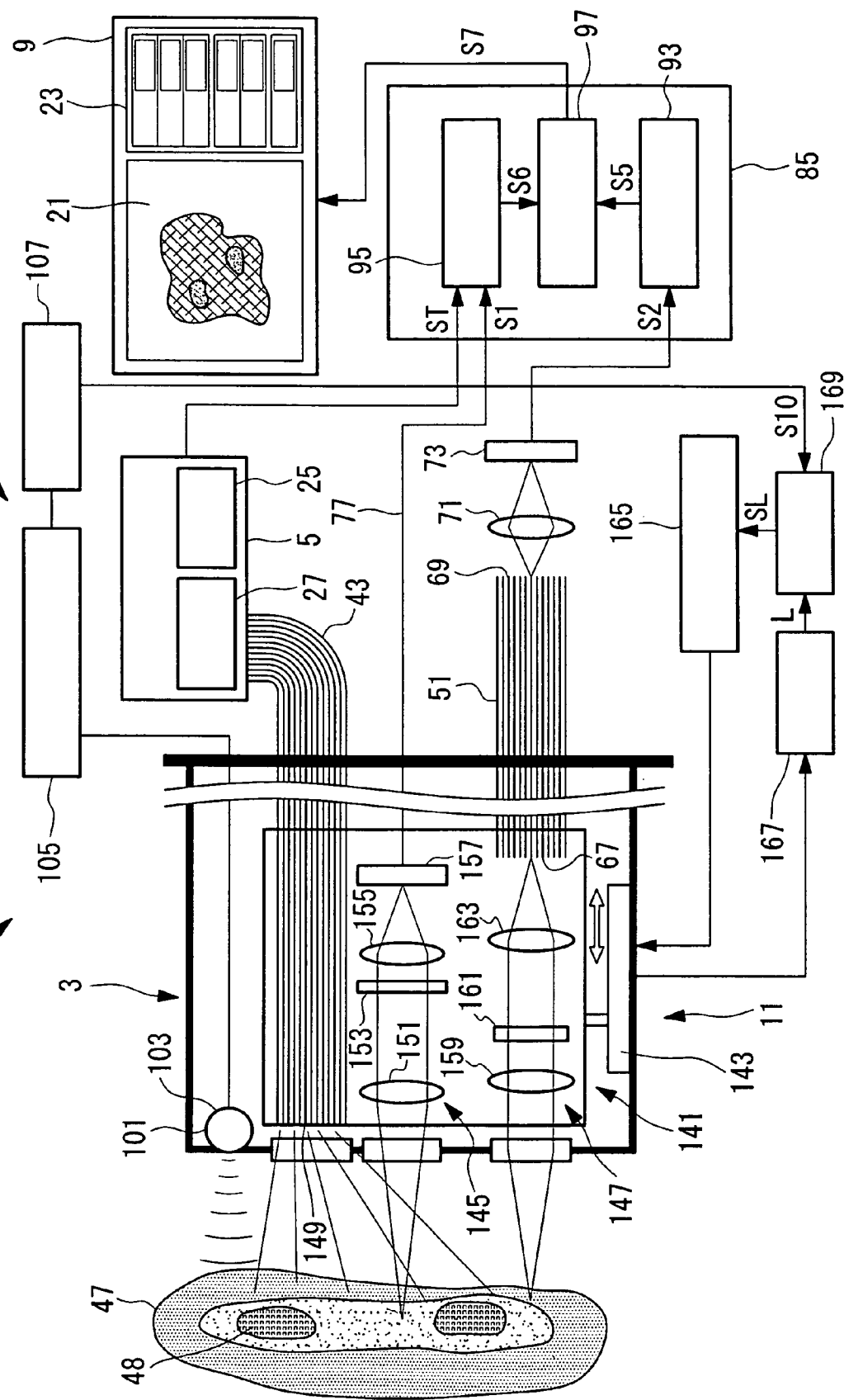
FIG. 11 is a block diagram depicting the overall structure of an endoscope apparatus according to a fourth embodiment of the present invention.

FIG. 11 is a block diagram depicting the overall outline structure of the endoscope apparatus 1 according to this embodiment.

The end portion in the insertion section 11 of the endoscopy scope 3 includes a distal optical system unit 141 supported so as to be movable in the optical-axis direction and an actuator 143 for driving the distal optical system unit 141 in the optical-axis direction.

An end of the illumination fiber bundle 43 is mounted on the distal optical system unit 141, which includes an illumination objective optical system 145 and a fluorescence objective optical system 147.

The end portion of the illumination fiber bundle 43 externally emits illumination light and excitation light from an irradiation section 149 formed at an end of the distal optical system unit 141.

The illumination objective optical system 145 includes a reflected-light objective lens 151 for receiving reflected light from the tissue 47 to convert it into collimated light, a barrier filter 153 for cutting light with wavelengths longer than those of excitation light, a reflected-light focusing lens 155 for focusing reflected light onto a CCD (reflected-light imaging unit) 157 to be described later, and the CCD 157 for converting the reflected light focused onto the imaging surface into an electrical signal to generate the reflected-light signal S1.

The fluorescence objective optical system 147 includes a fluorescence objective lens 159, an excitation light filter 161 for transmitting only fluorescence, and a fluorescence focusing lens 163. An end portion of the fluorescence fiber bundle 51 is mounted at the rear end of the distal optical system unit 141. The fluorescence focusing lens 163 focuses fluorescence onto one end 67 of the fluorescence fiber bundle 51.

Various types of linear actuators can be used as the actuator 143. The actuator 143 is driven by an actuator driving unit 165.

A position-detecting unit 167 tracks the movement of the distal optical system unit 141 to continuously detect a distance L between the ultrasound generator 101 and the irradiation section 149.

A displacement-calculating unit (distance-measuring unit) 169 calculates the distance between the tissue 47 and the irradiation section 149 based on the distance signal S10 from the distance-computing unit 107 and the distance L and outputs a distance signal SL to the actuator driving unit 165.

The actuator driving unit 165 drives the actuator 143 so that the difference between the distance signal SL and the predetermined distance becomes 0.

The image-processing unit 85 according to this embodiment does not include the amount-of-fluorescence calculating unit 109, which is included in the second embodiment. Therefore, the fluorescence image signal S5 is input directly to the superimposer 97.

The operation of the endoscope apparatus 1 with the above-described structure according to this embodiment will be described.

Administration of a chemical agent, irradiation of illumination light and excitation light, and display on the monitor 9 according to this embodiment are the same as those according to the first embodiment, and the calculation of the distance signal S10 based on an ultrasound signal according to this embodiment is the same as that according to the second embodiment. Thus, the description of these operations will be omitted.

The distance-computing unit 107 performs distance measurement using an ultrasound signal reflected back from the tissue 47 and outputs the distance signal S10. The distance-computing unit 107 then transmits this distance signal S10 to the displacement-calculating unit 169. The displacement-calculating unit 169 adds the distance signal S10 to the distance L from the position-detecting unit 167 to produce the distance signal SL and outputs it to the actuator driving unit 165. If the measured difference between the distance signal SL and the predetermined distance is not 0, the actuator driving unit 165 drives the actuator 143 in a direction for eliminating the difference, and the distal optical system unit 141 moves in the optical-axis direction accordingly. When this difference becomes 0, the actuator driving unit 165 stops driving the actuator 143.

Fluoroscopy is started in this state.

The irradiation section 149 irradiates illumination light and excitation light generated by the light source unit 5. Reflected light from the tissue 47 is converted into collimated light by the reflected-light objective lens 151 and passes through the barrier filter 153. At this time, light with wavelengths longer than those of the excitation light is cut from among the reflected light. Light that has not been cut by the barrier filter 153 is focused onto the CCD 157 by the focusing lens 155. In the CCD 157, the reflected light focused onto the imaging surface is converted into an electrical signal, which is the reflected-light signal S1. The reflected-light signal S1 is transmitted to the endoscopic-image generating unit 95 via the signal cable 77.

Furthermore, reflected light is converted into collimated light through the fluorescence objective lens 159, and only fluorescence of the reflected light passes through the excitation light filter 161. The fluorescence that has passed through the excitation light filter 161 is focused onto one end 67 of the fluorescence fiber bundle 51 by the fluorescence focusing lens 163.

This focused fluorescence is transmitted via the fluorescence fiber bundle 51, exits from the other end 69 of the fluorescence fiber bundle 51, and is focused onto the CCD 73 incorporating an imaging intensifier through the lens 71. In the CCD 73 incorporating an imaging intensifier, weak fluorescence is amplified to form an electrical signal, which is the fluorescence signal S2. The fluorescence signal S2 is transmitted to the fluorescence-image generating unit 93 via the signal cable 75.

The fluorescence-image generating unit 93 generates the fluorescence image signal S5 from the fluorescence signal S2. The fluorescence image signal S5 is input to the superimposer 97 together with the endoscopic image signal S6 generated in the endoscopic-image generating unit 95 to generate the superimposed-image signal S7.

The superimposed-image signal S7 generated by the superimposer 97 is output to the monitor 9 to display a composite image on the screen 21.

As described above, according to this embodiment, the displacement-calculating unit 169 generates the distance signal SL corresponding to the distance between the irradiation section 149 and the tissue 47. The actuator 143 moves the distal optical system unit 141 holding the end of the fluorescence fiber bundle 51 and the irradiation section 149 based on this distance signal SL, and thereby the distance between the irradiation section 149 and the tissue 47 is constantly maintained to be a certain value. Since fluoroscopy is performed with a certain distance constantly maintained between the irradiation section 149 and the tissue 47, as described above, quantitative diagnosis of a lesion can be made for improved diagnostic accuracy.

Fifth Embodiment

A fifth embodiment of the present invention will be described with reference to FIG. 12.

The basic structure of the endoscope apparatus 1 according to this embodiment is the same as that of the endoscope apparatus 1 according to the first embodiment, except for the mechanism for correcting the fluorescence signal S2.

The following description mainly focuses on this difference.

The same components in this embodiment as those used in the first embodiment are denoted by the same reference numerals, and thus will not be described.

Figure 12:
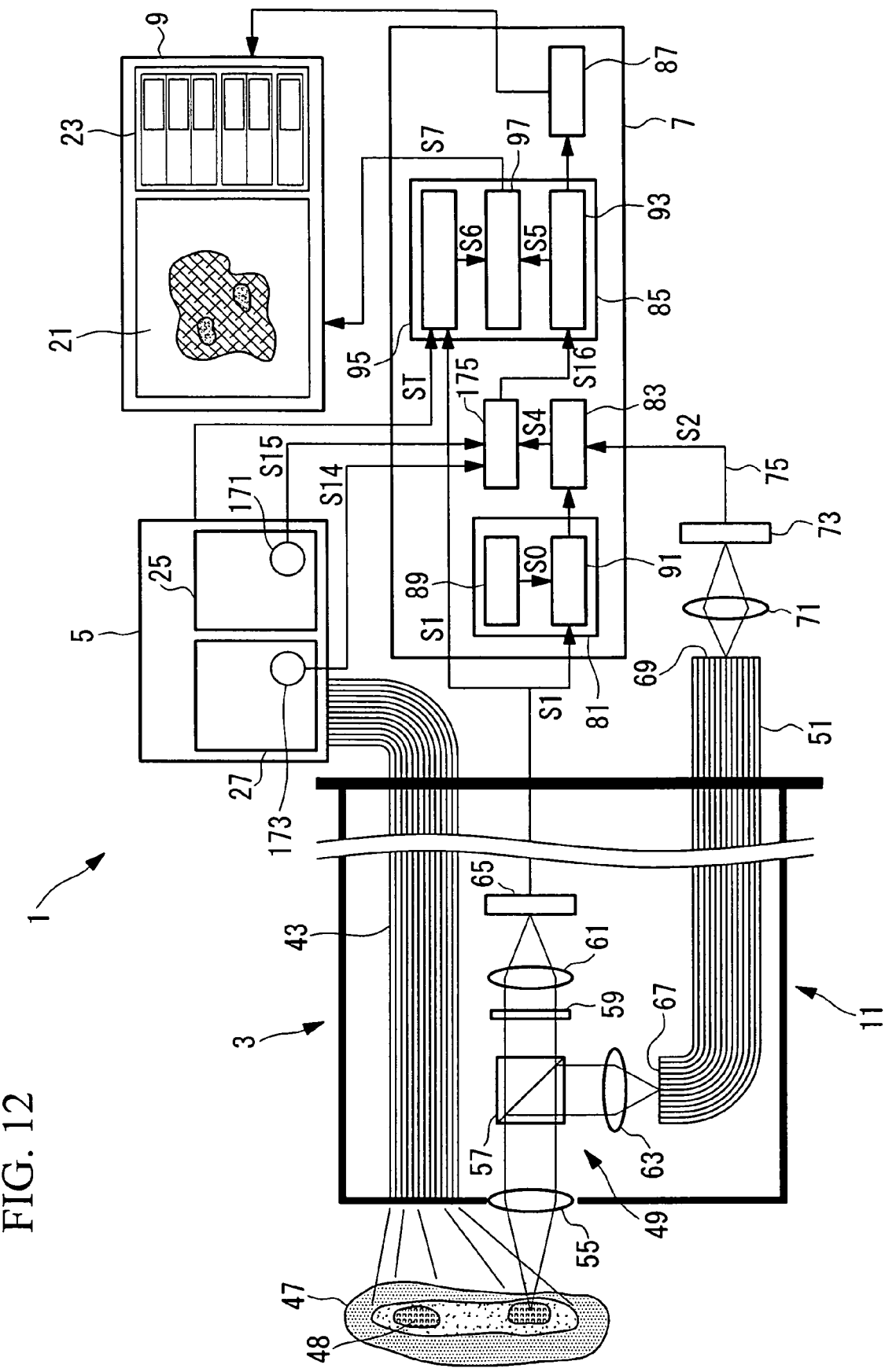
FIG. 12 is a block diagram depicting the overall structure of an endoscope apparatus according to a fifth embodiment of the present invention.

FIG. 12 is a block diagram depicting the overall outline structure of the endoscope apparatus 1 according to this embodiment.

The laser light source 25 includes an excitation-light-intensity measuring unit 171 for measuring the intensity of excitation light generated by the laser light source 25.

The white light source 27 includes an illumination-light intensity measuring unit 173 for measuring the intensity of illumination light generated by the white light source 27.

The image processor 7 includes a light-source-intensity-fluctuation correcting unit 175.

The light-source-intensity-fluctuation correcting unit 175 receives the corrected fluorescence signal S4 from the amount-of-fluorescence calculating unit 83, an excitation-light-intensity signal S15 from the excitation-light-intensity measuring unit 171, and an illumination-light-intensity signal S14 from the illumination-light intensity measuring unit 173.

In the light-source-intensity-fluctuation correcting unit 175, the corrected fluorescence signal S4 is divided by the excitation-light-intensity signal S15 and multiplied by the illumination-light-intensity signal S14 to calculate a fluctuation-corrected fluorescence signal S16, which is then transmitted to the fluorescence-image generating unit 93.

In the fluorescence-image generating unit 93, the fluorescence image signal S5 is generated from the fluctuation-corrected fluorescence signal S16, and a composite image is displayed on the screen 21 of the monitor 9 via the superimposer 97.

Since the measured fluorescence intensity is substantially proportional to the intensity of excitation light, the effects of fluctuation in excitation light can be eliminated by dividing the corrected fluorescence signal S4 by the excitation-light-intensity signal S15. On the other hand, in the distance calculating unit 91, the reflected-light intensity signal S0 at the predetermined distance is divided by the measured reflected-light signal S1. Since the reflected-light signal S1 is affected by fluctuations in the illumination light, the effects of fluctuation in the illumination light can be eliminated by multiplying the corrected fluorescence signal S4 by the illumination-light-intensity signal S14.

As described above, according to this embodiment, even if the light intensity of excitation light and illumination light fluctuates to cause, for example, the amount of fluorescence and reflected light to vary, the light-source-intensity-fluctuation correcting unit 175 corrects the corrected fluorescence signal S4 with the excitation-light-intensity signal S15 and the illumination-light-intensity signal S14. This suppresses the effects of fluctuation in the light intensity of the excitation light and the illumination light. Consequently, fluorescence can be measured with increased accuracy and accordingly the diagnostic accuracy is improved.

Applying such correction only to excitation light offers substantial effects as well because fluctuation in the excitation light has a large effect on the measurement accuracy.

Sixth Embodiment

A sixth embodiment according to the present invention will be described below with reference to FIGS. 13 and 14.

The basic structure of the endoscope apparatus 1 according to this embodiment is the same as that of the endoscope apparatus 1 according to the second embodiment, except for part of the structure of the amount-of-fluorescence calculating unit 109.

The following description mainly focuses on this difference.

The same components in this embodiment as those used in the second embodiment are denoted by the same reference numerals, and thus will not be described.

Figure 13:
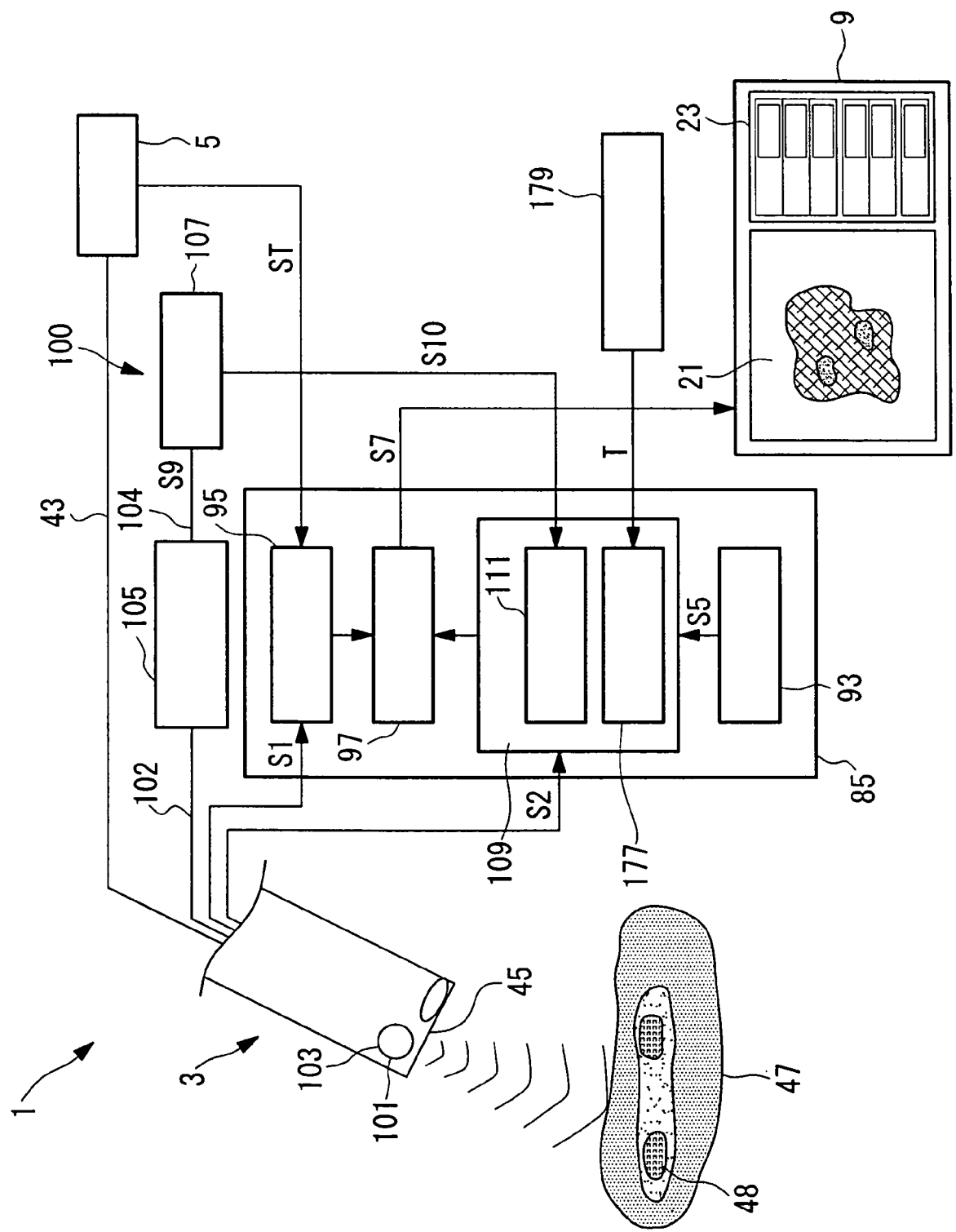
FIG. 13 is a block diagram depicting the overall structure of an endoscope apparatus according to a sixth embodiment of the present invention.

FIG. 13 is a block diagram depicting the overall outline structure of the endoscope apparatus 1 according to this embodiment. FIG. 14 is a typical correlation diagram depicting the relationship between the time elapsed after the administration of a chemical agent and the amount of accumulated chemical agent. As shown in FIG. 14, accumulation of a chemical agent exhibits the following typical change over time: the chemical agent starts to accumulate a certain time after the administration thereof, the amount of accumulation increases in proportion to the passing of time, and after the peak of accumulation continues for a certain period of time, the amount of accumulation starts to decrease.

The amount-of-fluorescence calculating unit 109 includes a post-administration-time correcting unit 177. The post-administration-time correcting unit 177 contains data representing a correlation diagram, as shown in FIG. 14, for each of various types of chemical agents. When a desired chemical agent is specified with a setting unit (not shown), the correlation diagram corresponding to that chemical agent can be selected.

A time-setting unit 179 is also provided to input a time signal T to the post-administration-time correcting unit 177 in response to time data entered by the operator.

The post-administration-time correcting unit 177 calculates the amount of accumulation (indicated as a percentage of the peak, assumed to be 1) of the chemical agent according to the time input from the time-setting unit 179 with reference to the selected correlation diagram and corrects the fluorescence image signal S5.

Figure 14:
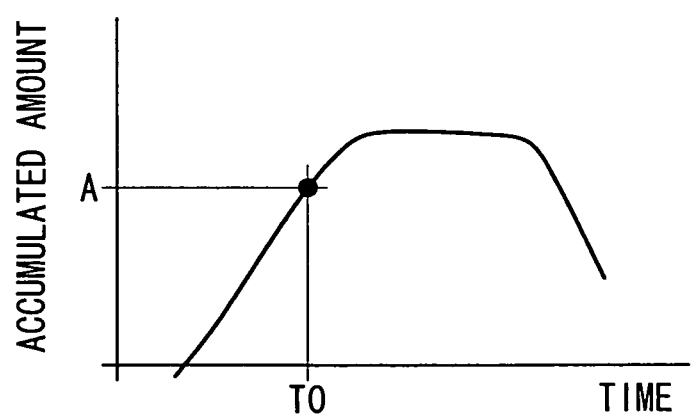
FIG. 14 is a correlation diagram depicting the relationship between the time elapsed after the administration of a chemical agent and the amount of accumulated chemical agent according to the sixth embodiment of the present invention.

For example, at the time T0 after the administration of the chemical agent as shown in FIG. 14, the fluorescence image signal S5 is divided by an accumulation percentage of A at the time T0 to correct the fluorescence image signal S5 to a signal as measured at the peak.

As described above, according to this embodiment, measurement can be started even before the administered fluorescence agent becomes sufficiently effective in the tissue 47 because the measurement is corrected to a value as measured when the agent is sufficiently circulated through the tissue 47. This is advantageous in making a quicker diagnosis. Furthermore, the diagnostic accuracy is improved.

Seventh Embodiment

A seventh embodiment of the present invention will be described with reference to FIGS. 15 to 17.

The basic structure of the endoscope apparatus 1 according to this embodiment is the same as that of the endoscope apparatus 1 according to the first embodiment. The seventh embodiment differs from the first embodiment in the structure of the distance-measuring unit, the structure of the end portion 45 of the insertion section 11, and the structure of the image-processing unit 85.

The description below mainly focuses on these differences.

The same components in this embodiment as those used in the first embodiment are denoted by the same reference numerals, and thus will not be described.

Figure 15:
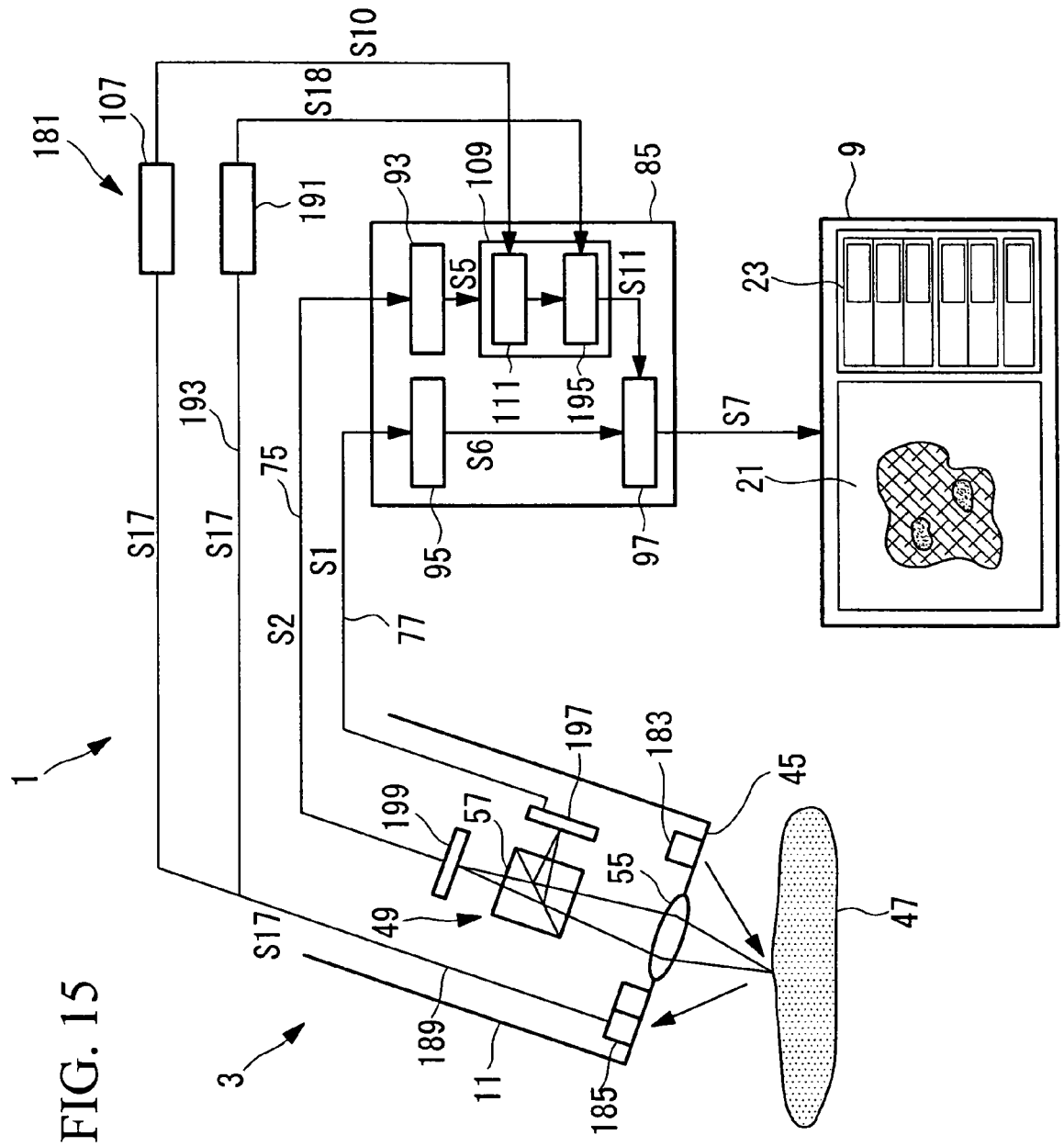
FIG. 15 is a block diagram depicting the overall structure of an endoscope apparatus according to a seventh embodiment of the present invention.
Figure 16:
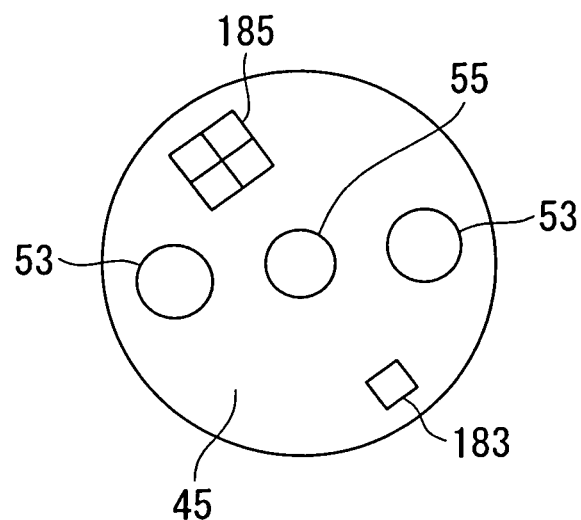
FIG. 16 is a front view of an end portion of an endoscopy scope according to the seventh embodiment of the present invention.

FIG. 15 is a block diagram depicting the overall outline structure of the endoscope apparatus 1 according to this embodiment. FIG. 16 is a front view of the end surface of the endoscopy scope 3.

A distance-measuring unit 181 of the endoscope apparatus 1 according to this embodiment will be described. The distance-measuring unit 181 includes a laser generator 183 and a laser beam detector 185 provided at the end portion 45 of the insertion section 11 of the endoscopy scope 3 and the distance-computing unit 107.

The laser generator 183 emits a laser beam with a power supply (not shown).

The laser beam detector 185 receives reflected laser light of the laser beam from the laser generator 183. It is realized by, for example, a split photodiode. Referring to FIG. 17, the end surface of the laser beam detector 185 is substantially rectangular, and is divided vertically and horizontally into a total of four divisions 187 each of which has substantially the same area. The laser generator 183 and the laser beam detector 185 are arranged such that the line connecting the laser generator 183 and the laser beam detector 185 passes through the objective lens 55 of the objective optical system 49.

The light source may be realized by an LED instead of the laser generator 183.

The laser beam detector 185 and the distance-computing unit 107 are connected with a signal cable 189.

The laser beam detector 185 emits a detection signal S17 from each of the divisions 187 in response to received light. The emitted detection signals S17 are transmitted to the distance-computing unit 107 via the signal cable 189.

In the distance-computing unit 107, the distance between the endoscopy scope 3 and the tissue 47 is calculated by comparing pre-obtained data and the average brightness of the detection signals S17 from the divisions 187.

The distance signal S10 calculated in the distance-computing unit 107 is transmitted to the distance-correcting unit 111.

The detection signals S17 are transmitted to an angle-calculating unit 191 via a signal cable 193 separated from the signal cable 189.

The angle-calculating unit 191 calculates the amounts of reflected laser light received at the divisions 187 of the laser beam detector 185 based on the signals S17 and calculates the tilt angle of the endoscopy scope 3 relative to the tissue 47 based on the deviation among them.

The angle signal S10 calculated by the angle-calculating unit 191 is transmitted to an angle-correcting unit 195.

According to this embodiment, there are provided two illumination fiber bundles 43 (not shown in the figure) via which illumination light and excitation light are transmitted. Referring to FIG. 16, the irradiation sections 53 for irradiating illumination light and excitation light transmitted via the illumination fiber bundles 43 are provided symmetrically with respect to the objective lens 55 of the objective optical system 49.

The objective optical system 49 includes the objective lens 55, the fluorescence filter 57 for separating fluorescence from normal reflected light excited by excitation light, a CCD 197 onto which light reflected at the fluorescence filter 57 is focused, and a CCD 199 onto which reflected light that has passes through the fluorescence filter 57 is focused.

The fluorescence filter 57 is an optical element that separates light coming through the objective lens 55 into fluorescence and reflected light by transmitting fluorescence-band light (light with a wavelength of 690 nm and its neighboring wavelengths), while reflecting light with other wavelengths at a right angle.

In the CCD 197, reflected light focused onto the imaging surface is converted into an electrical signal, which is the reflected-light signal S1. The reflected-light signal S1 is transmitted to the endoscopic-image generating unit 95 via the signal cable 77.

In the CCD 199, fluorescence focused onto the imaging surface is amplified and converted into an electrical signal, which the fluorescence signal S2. The fluorescence signal S2 is transmitted to the fluorescence-image generating unit 93 via the signal cable 75.

The image-processing unit 85 includes the amount-of-fluorescence calculating unit 109 between the fluorescence-image generating unit 93 and the superimposer 97.

In the fluorescence-image generating unit 93, the fluorescence image signal S5 is generated from the input fluorescence signal S2 and is output to the amount-of-fluorescence calculating unit 109.

The amount-of-fluorescence calculating unit 109 includes the distance-correcting unit 111 and the angle-correcting unit 195. The distance-correcting unit 111 corrects the fluorescence image signal S5 with the distance signal S10 from the distance-computing unit 107. The angle-correcting unit 195 corrects the fluorescence image signal S5 with an angle signal S18 from the angle-calculating unit 191. In this manner, the amount-of-fluorescence calculating unit 109 generates the corrected fluorescence-image signal S11.

The corrected fluorescence-image signal S11 is transmitted to the superimposer 97.

The operation of the endoscope apparatus 1 with the above-described structure according to this embodiment will be described.

The operations of administration of a chemical agent, irradiation of illumination light and excitation light, detection of reflected light and fluorescence, and display on the monitor 9 according to this embodiment are the same as those according to the first embodiment, and thus will not be described below.

Light transmitted from the light source unit 5 is irradiated onto the tissue 47 from the two irradiation sections 53 provided at the end portion 45.

Reflected light from the tissue 47 enters the objective lens 55, is reflected at the fluorescence filter 57, and is focused onto the CCD 197. In the CCD 197, reflected light focused onto the imaging surface is converted into an electrical signal, which is the reflected-light signal S1. The reflected-light signal S1 is transmitted to the endoscopic-image generating unit 95 via the signal cable 77. In the endoscopic-image generating unit 95, the endoscopic image signal S6 is generated from the reflected-light signal S1.

On the other hand, fluorochrome, such as 5-ALA or indocyanine-green-derivative-labeled antibodies, accumulated in cancer cells is excited by excitation light irradiated onto the tissue 47 from the irradiation sections 53 to generate fluorescence.

This fluorescence enters the objective lens 55 and is focused onto the CCD 199 through the fluorescence filter 57.

In the CCD 199, fluorescence is converted into an electrical signal, which is the fluorescence signal S2. The fluorescence signal S2 is transmitted to the fluorescence-image generating unit 93 via the signal cable 75. In the fluorescence-image generating unit 93, the fluorescence image signal S5 is generated from the fluorescence signal S2 and is transmitted to the amount-of-fluorescence calculating unit 109.

A laser beam emitted from the laser generator 183 is reflected at the tissue 47, and the laser beam reflected from the tissue 47 enters the laser beam detector 185.

Figure 17:
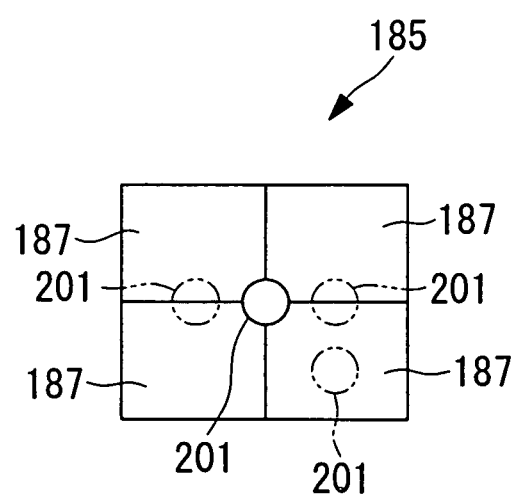
FIG. 17 is a front view of a laser beam detector according to the seventh embodiment of the present invention.

At this time, if the endoscopy scope 3 is exactly opposite the tissue 47, i.e., if the endoscopy scope 3 is not angled with respect to the tissue 47, then the amounts of light received at the divisions 187 are substantially the same because a center 201 of the reflected laser beam is located at the center of the laser beam detector 185, as shown by a solid line in FIG. 17.

On the other hand, if the endoscopy scope 3 is angled with respect to the tissue 47, then the amounts of light received at the divisions 187 are different because the center 201 of the reflected laser beam is shifted from the center of the laser beam detector 185 to a position depending on the tilting, as shown by broken lines in FIG. 17.

The laser beam detector 185 transmits the amounts of light received at these divisions 187 to the distance-computing unit 107 and the angle-calculating unit 191 as the detection signals S17.

In the distance-computing unit 107, the average amount of light or the total amount of light is calculated based on the detection signals S17 from the divisions 187, and the distance between the endoscopy scope 3 and the tissue 47 is calculated from the pre-obtained calibration data to generate the distance signal S10.

In the angle-calculating unit 191, the tilt angle of the endoscopy scope 3 relative to the tissue 47 is calculated using the detection signals S17 from the divisions 187. For example, since the amount of received light is inversely proportional to the square of the distance, the difference between amounts of received light represents the difference between the corresponding distances. From the ratios among the amounts of received light at the divisions 187, distance relationships are calculated, and the tilting of the endoscopy scope 3 is calculated from these distance relationships. Based on this tilting, the tilt angle of the endoscopy scope 3 is calculated to generate the angle signal S18.

The distance signal S10 and the angle signal S18 generated in the distance-computing unit 107 and the angle-calculating unit 191 are transmitted to the amount-of-fluorescence calculating unit 109.

In the amount-of-fluorescence calculating unit 109, the distance-correcting unit 111 and the angle-correcting unit 195 correct the fluorescence image signal S5 with the distance signal S10 and the angle signal S18 to generate the corrected fluorescence-image signal S11.

The corrected fluorescence-image signal S11, as well as the endoscopic image signal S6 generated in the endoscopic-image generating unit 95 is input to the superimposer 97 to generate the superimposed-image signal S7.

The superimposed-image signal S7 generated by the superimposer 97 is output to the monitor 9 to display a composite image on the screen 21.

As described above, according to this embodiment, the fluorescence image signal S5 generated from the fluorescence signal S2 indicating the amount of fluorescence is corrected with the distance signal S10 and the angle signal S18 to generate the corrected fluorescence-image signal S11 not influenced by the distance to the tissue 47 and of the tilt angle of the endoscopy scope 3.

Since a fluorescence image is displayed on the monitor 9 based on this corrected fluorescence-image signal S11, the amount of fluorescence not influenced by the distance between the irradiation section 53 and the tissue 47 and tilting of the endoscopy scope 3 is displayed on the monitor 9.

As described above, since the amount of fluorescence not influenced by the distance between the irradiation section 53 and the tissue 47 and tilting of the endoscopy scope 3 is displayed, quantitative diagnosis of a lesion can be made for improved diagnostic accuracy.

Figure 18:
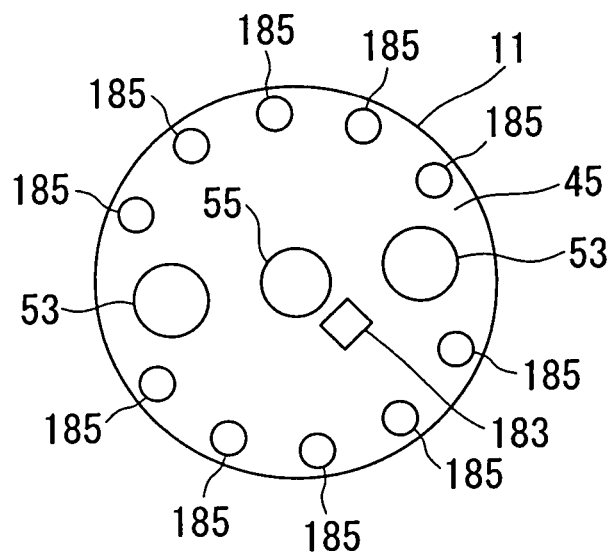
FIG. 18 is a front view of another example of the endoscopy scope according to the seventh embodiment of the present invention.
Figure 19:
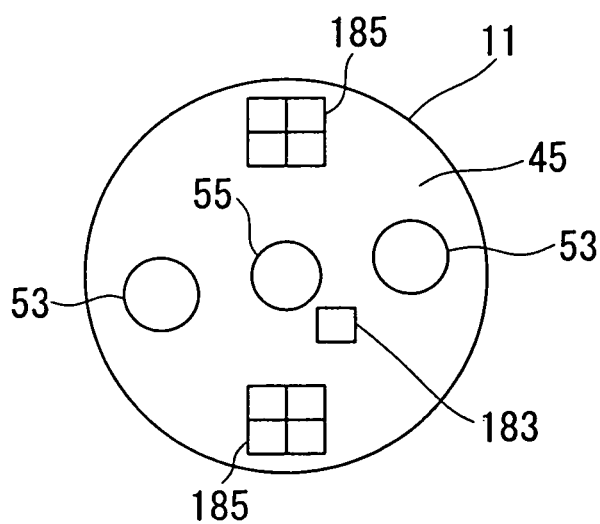
FIG. 19 is a front view of still another example of the endoscopy scope according to the seventh embodiment of the present invention.

Although in this embodiment one laser generator 183 corresponds to one laser beam detector 185, a plurality of laser beam detectors 185 may be provided for one laser generator 183, as shown in FIGS. 18 and 19.

FIG. 18 shows one laser generator 183 being disposed near the center of the end portion 45 of the endoscopy scope 3 and a plurality of substantially circular laser beam detectors 185 spaced out at the perimeter of the end portion 45 in the circumferential direction.

With this structure, the proportions among the amounts of light received at the laser beam detectors 185 can be detected more clearly. This is advantageous in calculating the tilt angle of the endoscopy scope 3 more accurately.

FIG. 19 shows two laser beam detectors 185 according to this embodiment with their light receiving surfaces each divided into four divisions and being disposed symmetrically with respect to the objective lens 55. The laser generator 183 is disposed near the center of the end portion 45 of the endoscopy scope 3.

With this structure, reflected laser beams can be detected uniformly. This is advantageous in calculating the tilt angle of the endoscopy scope 3 more accurately.

Although in this embodiment the distance is calculated based on the amounts of reflected laser light incident upon the divisions 187, the distance may be calculated based on the reflection time.

Furthermore, although in this embodiment a laser beam is used for the distance-measuring unit 181, the present invention is not limited to a laser beam. For example, the present invention may be realized in the manner as described in the first embodiment to the sixth embodiment.

Furthermore, although in this embodiment a laser beam is used for the angle-calculating unit 191, the present invention is not limited to a laser beam. Instead, for example, microwaves or ultrasound may be used.

Eighth Embodiment

An eighth embodiment of the present invention will be described with reference to FIGS. 20 and 21.

The basic structure of the endoscope apparatus 1 according to this embodiment is the same as that of the endoscope apparatus 1 according to the seventh embodiment. Thus, the description below mainly focuses on differences from the seventh embodiment.

The same components in this embodiment as those used in the seventh embodiment are denoted by the same reference numerals, and thus will not be described.

Figure 20:
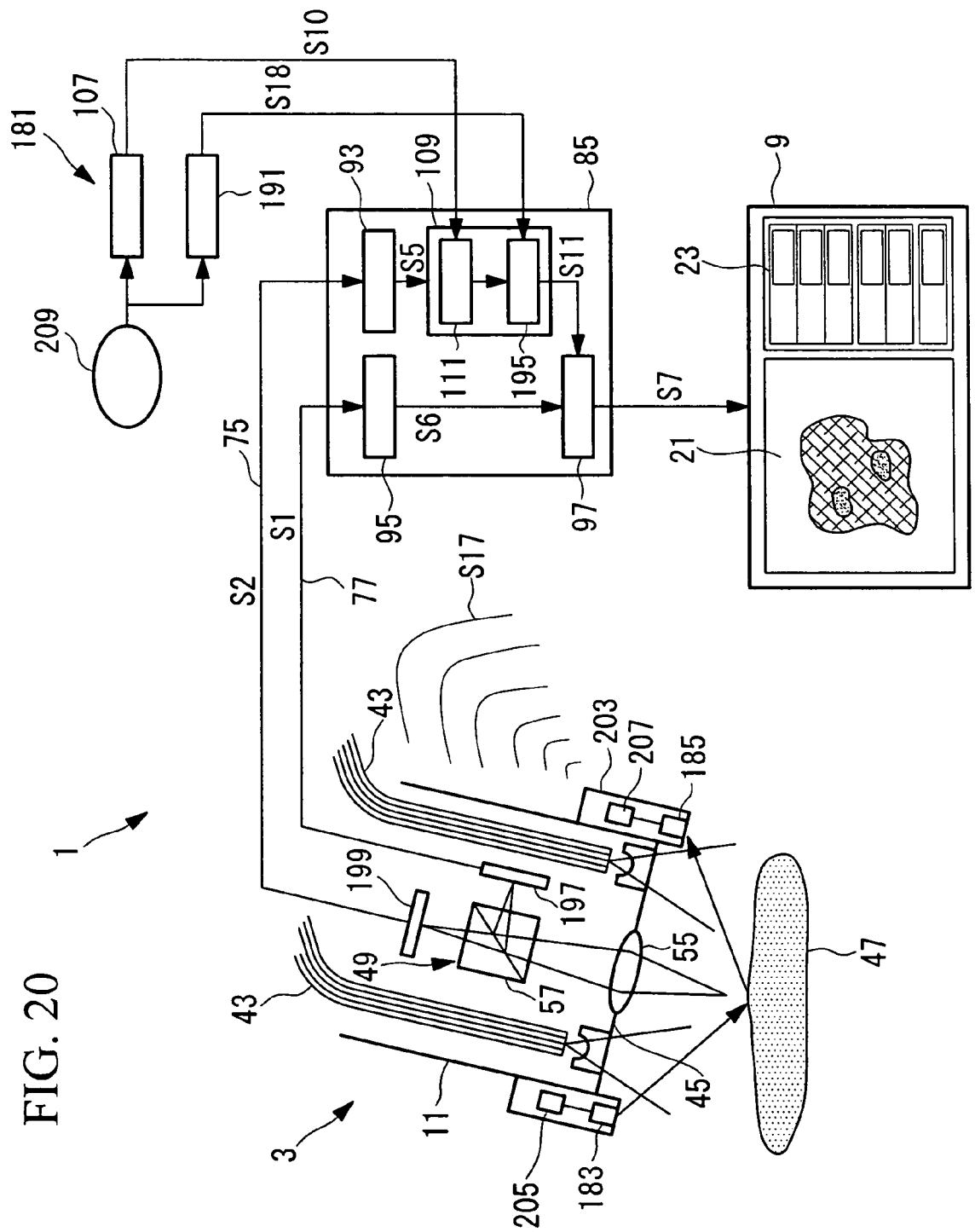
FIG. 20 is a block diagram depicting the overall structure of an endoscope apparatus according to an eighth embodiment of the present invention.
Figure 21:
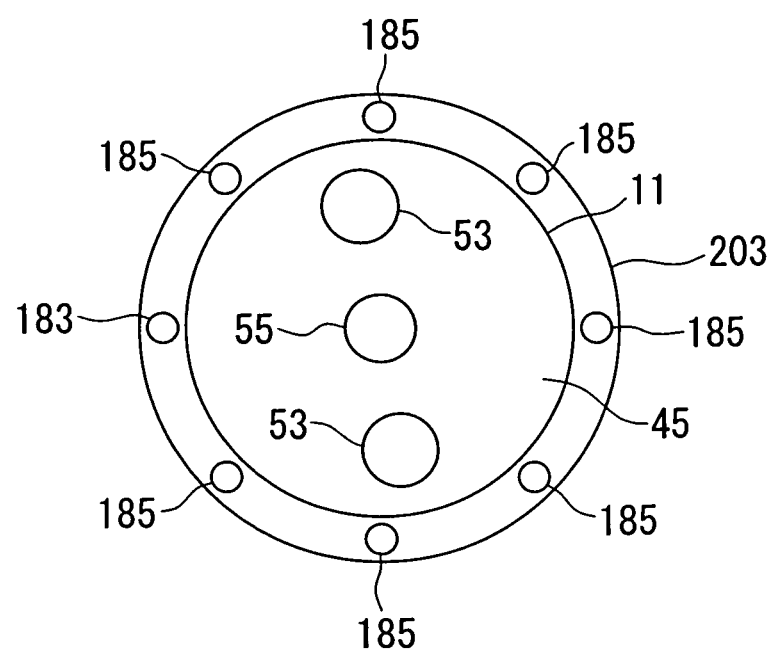
FIG. 21 is a front view of an end portion of an endoscopy scope according to the eighth embodiment of the present invention.

FIG. 20 is a block diagram depicting the overall outline structure of the endoscope apparatus 1 according to this embodiment. FIG. 21 is a front view of the end surface of the endoscopy scope 3.

According to this embodiment, the endoscopy scope 3 has a detachable cap 203 at the perimeter of the end portion 45.

The cap 203 is toroidal, and has on its end surface the laser generator 183 and a plurality of the laser beam detectors 185 spaced out at substantially equal intervals in the circumferential direction.

The cap 203 has a laser power supply 205, which is connected to the laser generator 183.

The light source may be realized by an LED instead of the laser generator 183.

A signal transmitter 207 in the cap 203 is connected to each of the laser beam detectors 185.

The laser beam detectors 185 generate the detection signals S17 from received light. The generated detection signals S17 are emitted from the signal transmitters 207.

The image processor 7 includes a signal receiver 209 for receiving these detection signals.

The detection signals S17 received by the signal receiver 209 are transmitted to the distance-computing unit 107 and the angle-calculating unit 191 via a signal cable.

As described above, since the laser generator 183 and the laser beam detectors 185 are provided in the cap 203, which is detachably mounted on the external surface of the endoscopy scope 3, modification in the endoscopy scope 3 is not necessary.

Therefore, not only can a drastic design change of the endoscopy scope 3 be avoided, but the laser generator 183 and the laser beam detectors 185 can easily be mounted on an existing endoscopy scope 3.

Ninth Embodiment

A ninth embodiment of the present invention will be described with reference to FIGS. 22 to 24.

The basic structure of the endoscope apparatus 1 according to this embodiment is the same as that of the endoscope apparatus 1 according to the seventh embodiment, except for a signal used for calculation in the distance-computing unit 107 and angle-calculating unit 191.

The description below mainly focuses on this difference.

The same components in this embodiment as those used in the seventh embodiment are denoted by the same reference numerals, and thus will not be described.

Figure 22:
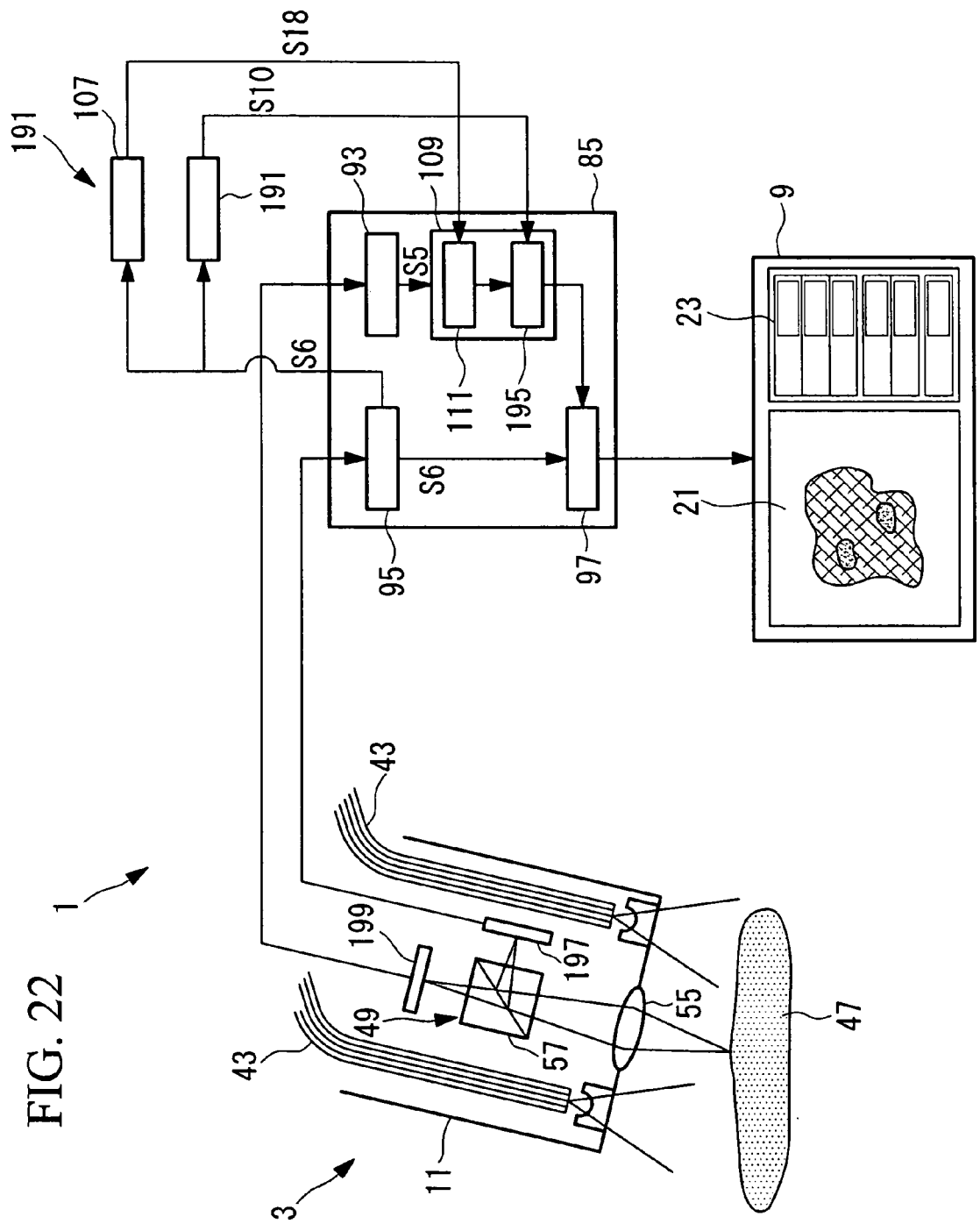
FIG. 22 is a block diagram depicting the overall structure of an endoscope apparatus according to a ninth embodiment of the present invention.
Figure 23:
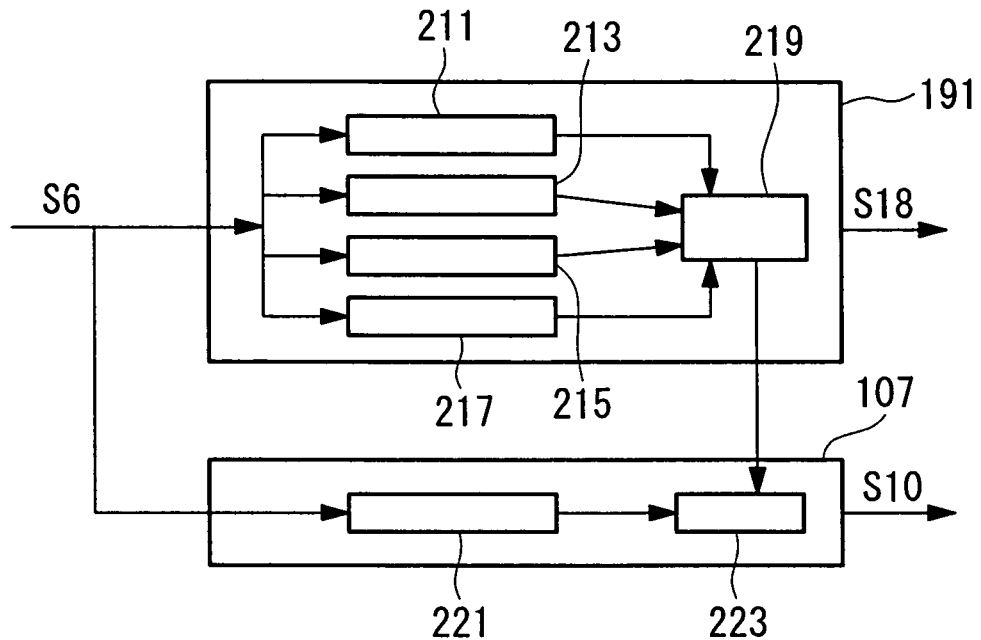
FIG. 23 is a block diagram depicting the structure of an angle-calculating unit according to the ninth embodiment of the present invention.

FIG. 22 is a block diagram depicting the overall outline structure of the endoscope apparatus 1 according to this embodiment. FIG. 23 is a block diagram depicting the outline structures of the distance-computing unit 107 and the angle-calculating unit 191. FIG. 24 is a front view of the monitor 9 showing an example display on the screen 21.

According to this embodiment, the endoscopic image signal S6 is used as a signal for calculation in the distance-computing unit 107 and the angle-calculating unit 191.

In the angle-calculating unit 191, the screen is divided into a plurality of areas, e.g., four areas A, B, C, and D, and the endoscopic image signal S 6 is divided into four signal components corresponding to areas A, B, C, and D, respectively.

The angle-calculating unit 191 includes an A-calculating unit 211 for calculating the average brightness of area A, a B-calculating unit 213 for calculating the average brightness of area B, a C-calculating unit 215 for calculating the average brightness of area C, a D-calculating unit 217 for calculating the average brightness of area D, and an angle-determining unit 219.

The angle-determining unit 219 determines the angle in the typical manner described below.

Figure 24:
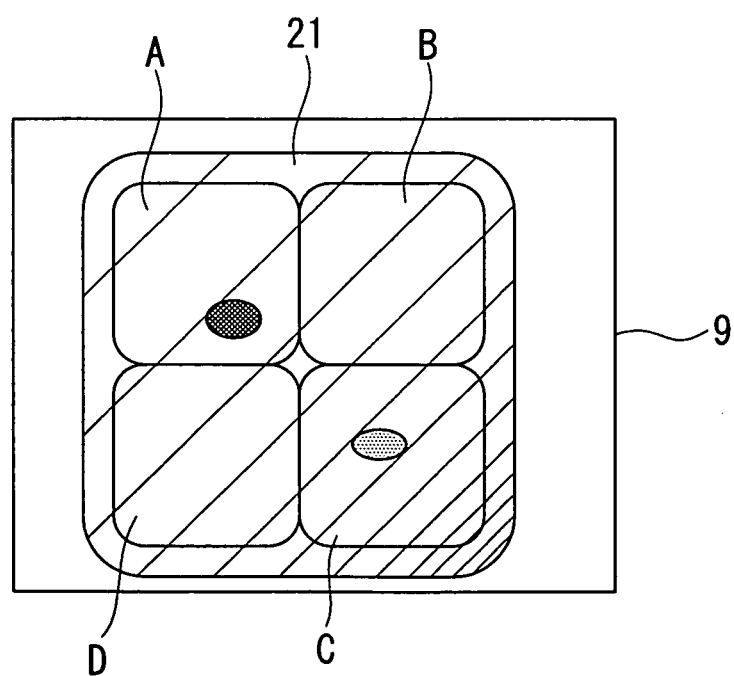
FIG. 24 is a front view of a monitor according to the ninth embodiment of the present invention.

If it is assumed that a reflected light image in area A is brighter than that in area C, as shown in FIG. 24, this means that the end portion 45 of the endoscopy scope 3 is relatively close to the site corresponding to area A and is relatively remote from the site corresponding to area C.

Since the brightness is inversely proportional to the square of the distance, relative relationships among distances can be calculated from the average brightnesses of the areas A, B, C, and D. The tilt angle of the endoscopy scope 3 can be calculated from these distance relationships.

In addition, calibration data for the brightness distribution in areas A, B, C, and D measured with various types of endoscopy scopes 3 being tilted can be prepared, so that the tilt angle corresponding to the calculated brightness distribution in the areas A, B, C, and D may be selected.

The distance-computing unit 107 includes an average-calculating unit 221 for calculating the average brightness of totally reflected light and a distance determining unit 223.

Assuming that the incident angle on the objective lens 55 is constant, the endoscopy scope 3 causes the screen to become more dark when it is tilted than when it is not tilted, even with the same distance being maintained, because the endoscopy scope receives reflected light along a longer distance when tilted. In short, despite the same brightness, when the endoscopy scope 3 is angled relative to the tissue 47, the distance to the tissue 47 becomes longer.

The distance determining unit 223 determines the distance based the average brightness of totally reflected light calculated by the average-calculating unit 221 and the tilt angle determined by the angle-determining unit 219.

According to this embodiment, in addition to the operations and advantages according to the seventh embodiment, the distance between the irradiation section 53 and the tissue 47 and the tilt angle of the endoscopy scope 3 are obtained based on reflected light, and hence devices for obtaining these measurements are omitted. This allows the structure of the endoscopy scope 3 to be simplified, and accordingly the endoscopy scope 3 to be manufactured at low cost.

What is claimed is:
1. An endoscope apparatus comprising:
a light source unit including at least one light source generating illumination light and excitation light;
an endoscopy scope including, at an end portion thereof, an irradiation section for irradiating the illumination light and the excitation light;
a reflected-light imaging unit for detecting reflected light generated as a result of the illumination light being reflected at a tissue;

an endoscopic-image generating unit for generating an endoscopic image signal based on a reflected-light signal from the reflected-light imaging unit;

a fluorescence-detecting unit for detecting fluorescence generated in the tissue by the excitation light;

a fluorescence-image generating unit for generating a fluorescence image signal based on a fluorescence signal from the fluorescence-detecting unit;

a ratio-generating unit that generates a ratio between an intensity of the reflected-light signal and an intensity of the reflected light that has been determined in advance from a predetermined distance; and a correcting unit for correcting the fluorescence signal or the fluorescence image signal with the ratio and generating a corrected fluorescence signal or a corrected fluorescence image signal that is not influenced by changes in the distance between the irradiation section and the tissue.

2. The endoscope apparatus according to claim 1, further comprising:

an amount-calculating unit for calculating an amount of target substance based on an amount of fluorescence from the corrected fluorescence image signal.

3. The endoscope apparatus according to claim 1, further comprising:

an image-size calculating unit that calculates a corrected image size.

4. The endoscope apparatus according to claim 1, further comprising:

an image superimposing unit for combining the endoscopic image signal and the fluorescence image signal.

5. The endoscope apparatus according to claim 1, wherein the ratio-generating unit uses light.

6. The endoscope apparatus according to claim 5, wherein the light is a laser beam.

7. The endoscope apparatus according to claim 1, further comprising:

an angle-calculating unit for calculating an angle of the endoscopy scope relative to the tissue.

8. The endoscope apparatus according to claim 7, wherein the angle-calculating unit uses ultrasound.

9. The endoscope apparatus according to claim 7, wherein the angle-calculating unit uses microwaves.

10. The endoscope apparatus according to claim 7, wherein the angle-calculating unit uses light.

11. The endoscope apparatus according to claim 10, wherein the light is a laser beam.

12. The endoscope apparatus according to claim 1, wherein the correcting unit includes a post-administration-time correcting unit for correcting the fluorescence signal or the fluorescence image signal based on a time elapsed after administration of a fluorescence agent.

13. The endoscope apparatus according to claim 1, further comprising:

a light intensity measuring unit for measuring the intensity of the light source emitting the excitation light; and a light-source-intensity-fluctuation correcting unit for correcting the fluorescence signal or the fluorescence image signal based on the light intensity of the light source emitting the excitation light.

14. The endoscope apparatus according to claim 1, further comprising:

a display unit displaying an image with different visual effects depending on a fluorescence intensity.

15. An endoscope apparatus comprising:

a light source unit including at least one light source generating illumination light and excitation light;

an endoscopy scope having, at an end portion thereof, an irradiation section for irradiating the illumination light and the excitation light;

a reflected-light imaging unit for detecting reflected light generated as a result of the illumination light being reflected at a tissue;

an endoscopic-image generating unit for generating an endoscopic image signal based on a reflected-light signal from the reflected-light imaging unit;

a fluorescence-detecting unit for detecting fluorescence generated in the tissue by the excitation light;

a fluorescence-image generating unit for generating a fluorescence image signal based on a fluorescence signal from the fluorescence-detecting unit;

a ratio-generating unit that generates a ratio between an intensity of the reflected-light signal and an intensity of the reflected light that has been determined in advance from a predetermined distance;

a distal optical system unit for supporting an end portion of a transmitting member for transmitting the fluorescence to the fluorescence-detecting unit and the irradiation section, the distal optical system unit being provided so as to be movable along an optical-axis with respect to the irradiation section; and a driving unit for moving the distal optical system unit according to the ratio from the ratio-generating unit in such a way that the amount of excitation light irradiated per unit area on the tissue is not influenced by changes in the distance between the irradiation section and the tissue.

16. The endoscope apparatus according to claim 15, further comprising:

an image superimposing unit for combining the endoscopic image signal and the fluorescence image signal.

17. The endoscope apparatus according to claim 15, wherein the ratio-generating unit uses light.

18. The endoscope apparatus according to claim 17, wherein the light is a laser beam.

19. The endoscope apparatus according to claim 15, further comprising:

an angle-calculating unit for calculating an angle of the endoscopy scope relative to the tissue.

20. The endoscope apparatus according to claim 19, wherein the angle-calculating unit uses ultrasound.

21. The endoscope apparatus according to claim 19, wherein the angle-calculating unit uses microwaves.

22. The endoscope apparatus according to claim 19, wherein the angle-calculating unit uses light.

23. The endoscope apparatus according to claim 22, wherein the light is a laser beam.

24. The endoscope apparatus according to claim 15, further comprising:

a light-source-intensity-fluctuation correcting unit for correcting the fluorescence signal or the fluorescence image signal based on a light intensity of the light source emitting the excitation light.

25. An endoscope apparatus comprising:

a light source unit including at least one light source generating illumination light and excitation light;

an endoscopy scope including, at an end portion thereof, an irradiation section for irradiating the illumination light and the excitation light;

a reflected light detector for detecting reflected light generated as a result of the illumination light being reflected at a tissue;

an endoscopic image generating processor for generating an endoscopic image signal based on a reflected light signal from the reflected light detector;

a fluorescence detector for detecting fluorescence generated in the tissue by the excitation light;

a fluorescence image generating processor for generating a fluorescence image signal based on a fluorescence signal from the fluorescence detector;

a ratio generating processor that generates a ratio between an intensity of the reflected-light signal and an intensity of the reflected light that has been determined in advance from a predetermined distance; and a correcting processor for correcting the fluorescence signal or the fluorescence image signal with the ratio and for generating a corrected fluorescence signal or a corrected fluorescence image signal that is not influenced by changes in the distance between the irradiation section and the tissue.

26. An endoscope apparatus comprising:

a light source unit including at least one light source generating illumination light and excitation light;

an endoscopy scope having, at an end portion thereof, an irradiation section for irradiating the illumination light and the excitation light;

a reflected light detector for detecting reflected light generated as a result of the illumination light being reflected at a tissue;

an endoscopic image generating processor for generating an endoscopic image signal based on a reflected light signal from the reflected light detector;

a fluorescence detector for detecting fluorescence generated in the tissue by the excitation light;

a fluorescence image generating processor for generating a fluorescence image signal based on a fluorescence signal from the fluorescence detector;

a ratio generating processor for generating a ratio between an intensity of the reflected light signal and an intensity of the reflected light that has been determined in advance from a predetermined distance;

a distal optical system supporting mechanism for supporting an end portion of a transmitting member for transmitting the fluorescence to the fluorescence detector and the irradiation section, the distal optical system supporting mechanism being provided so as to be movable along an optical-axis with respect to the irradiation section; and a moving mechanism for moving the distal optical system supporting mechanism according to the ratio from the ratio generating processor in such a way that the amount of excitation light irradiated per unit area on the tissue is not influenced by changes in the distance between the irradiation section and the tissue.

* * * * *